United States Patent
Chau

(10) Patent No.: US 6,309,877 B1
(45) Date of Patent: Oct. 30, 2001

(54) POLYNUCLEOTIDES ENCODING MOTONEURONOTROPHIC FACTORS

(75) Inventor: Raymond Ming Wah Chau, Hong Kong (CN)

(73) Assignee: KM Biotech, Inc., Montebello, CA (US)

( * ) Notice: Subject to any disclaimer, the term of this patent is extended or adjusted under 35 U.S.C. 154(b) by 0 days.

(21) Appl. No.: 08/928,862

(22) Filed: Sep. 12, 1997

Related U.S. Application Data

(63) Continuation of application No. 08/751,225, filed on Nov. 15, 1996, now abandoned.
(60) Provisional application No. 60/026,792, filed on Sep. 27, 1996.

(51) Int. Cl.[7] ............................ C12N 15/18; C12N 15/63; C12N 15/85
(52) U.S. Cl. .................. 435/325; 435/320.1; 435/252.3; 536/23.51; 536/23.1
(58) Field of Search .............................. 536/23.51, 24.31, 536/23.1; 435/320.1, 325, 252.3

(56) References Cited

PUBLICATIONS

Chentret et al. Biochem. J. 285: 915–923, 1995.*
Rudinger, In "Peptide Hormones" (ed. J. A. Parsons) University Park Press, Baltimore, pp. 1–7, 1976.*
Chau, R.M.W. et al.: "Biological effect of motoneuronotrophic factor on wobbler mice with motoneuron disease" 26th Annual Meeting of the Society for Neuroscience, vol. 22, No. 1–3, Nov. 16–21, 1996, Washington, D.C., USA, p. 233 XP002067887, Abstract only.
Chau, R.M.W. and Jen, L.S.; Muscle neuronotrophic factors specific for anterior horn motoneurons of rat spinal cord. In: Recent Advances In Cellular And Molecular Biology. Wegmann, R.J. and Wegmann, M.A. (Eds), Peeters Press, Leuven, Belgium, 1992, vol. 5, pp. 89–94.
Chau, R.M.W. et al.: "Cloning of genes for muscle–derived motoneuronotrophic factor 1 (MNTF1) and its receptor by monclonal antibody probes," Society for Neuroscience Abstracts, vol. 19, 1993, p. 252 XP002067890, Abstract only.
Nomura et al., EMBL Database: EMHUM1:HSORFD1; Accession–No.: D21163, Dec. 15, 1993, XP002067891.
Auffray et al., EMBL Database; EMEST9:HSC38G051; Accession No.: F12338, Mar. 4, 1995, XP002067892.
Ming–Hua, Z. et al. Effect of 22kD, 35kD protein molecules from extract of skeletal muscle on cultured anterior horn motoneuron of lumbar spine in rat. Chinese Science Bulletin, (1992) 37(2):1742–46.
Minghua, Z., Chau, R.M.W., Ren, F., Huang, W.Q., Ren, L. Production and assessment of monoclonal antibodies specific for the 35kD motoneuronotrophic factor from rat skeletal muscle. Journal of Monoclonal Antibody, 1992, vol. 8(3), Abstract only.
Ming–Hua, Z. (Chau RMW), Yu, W., Ren, F. Changes in moto–neuronotrophic factor and its receptor in tongue muscle post–denervation of the hypoglossal nerve. Department of Anatomy, University of Hong Kong; Department of Cell Biology and Anatomical Sciences, City University of New York Medical School, New York, USA, 1993, 391–395, Abstract only.
Wang, A., Chau, R.M.W., Zhou, Z. et al. Effects of myogenic 22.35kD neurotrophic factors on axonal regeneration in free peripheral nerve auto–grafts implanted into rat spinal cord. Chinese Journal of Spine and Spinal Cord, 1995, 5(6):248, Abstract only.
Yu, W.H.A., Chau, R.M.W. and Ren, F. Muscle–derived motoneuronotrophic factors promote survival of axotomized motoneurons of the facial nerve. Abstracts, Society for Neuroscience, 22nd Annual Meeting 1992, 546.15, Abstract only.
Zhou, Ming–Hua, Ren, Feng and Zhao, Li–Ping. Indentification of a 12.5–kD Protein From Caudate–Putamen Nucleus as a Dopaminergic Neuronotrophic Factor. Science in China (Series B) vol. 37(11):1360–1365.
Chau, R.M.W., Ren, F. and Huang, W.Q. Programmed Cell Death of Neonatal Rat Retinal Ganglion Cells due to Turn–Off Expression of a Novel 30–kD Trophic Factor and/or the Lack of this Factor Supplied from the Superior Colliculus. Department of Anatomy, University of Hong Kong, Hong Kong. Aging and Cellular Mechanisms, vol. 663 of the Annals of the New York Academy of Sciences, Nov. 21, 1992, pp. 100–107.

* cited by examiner

*Primary Examiner*—Gary L. Kunz
*Assistant Examiner*—Robert C. Hayes
(74) *Attorney, Agent, or Firm*—Sheldon & Mak; David A. Farah, M.D.; James W. Collett

(57) ABSTRACT

An isolated polynucleotide encoding motoneuronotrophic factor F6.

12 Claims, 34 Drawing Sheets

```
CGGGCTTATT ATTCCACTGA TGAGAACCTG ATCCTTTCCC CACTCCTGGG TAACGTCTGC
TTCTCCAGCT CCCAGTACAG CATCTGCTTC ACGCTGGGCT CCTTTGCCAA GATCTATGCC
GACACCTTTG GTGACATTAA TTACCAAGAA TTTGCTAAAA GACTCTGGGG TGACATCTAC
TTCAACCCTA AGACGCGAAA GTTCACCAAA AAGGCCCCAA CTAGCAGCTC CAGAGAAGT
TTCGTGGAGT TTATCTTGGA GCCTCTTTAT AAGATCCTCG CCCAGGTTGT AGGTGACGTG
GACACCAGCC TCCCACGGAC CCTAGACGAG CTTGGCATCC ACCTGACGAA GGAGGAGCTG
AAGCTGAACA TCCGCCCCTT GCTCAGGCTG GTCTGCAAAA AGTTCTTTGG CGAGTTCACA
GGCTTTGTGG ACATGTGTGT GCAGCATATC CCTTCTCCAA AGGTGGGCGC CAAGCCCAAG
ATTGAGCACA CCTACACCGG TGGTGTGGAC TCCGACCTCG GCGAAGCTAT GAGTGACTGT
GACCCTGATG GCCCCCTGAT GTGCCACACT ACTAAGATGT TCAGCACACA TGATGGAGTC
CAGTTTCACC CCTTTGGCCG GGTGCTGAGT GGCACCATTC ATGCTGGGCA GCCTGTGAAG
GTTCTGGGGG AGAACTACAC CCTGGAGGAT GAGGAAGACT CCCCAATTTG CCCCGTGGGC
CGCCTTTGGA TCTCTGTGGC CAGCTACCAC ATCGAGGTGA ACCGTGTTCC TGCTGGCAAC
TGGGTTCTGA TTGAAGGTGT TGATCAACCA ATTGTGAAGA CAGCAACCAT AACCGAACCC
CGAGGCAATG AGGAGGCTCA GATTTTCCGA CCCTTGAAGT TCAATACCAC ATCTGTTATC
AAGATTGCTG TGGAGCCAGT CAACCCCTCA GAGCTGCCCA AGATGCTTGA TGGCCTGCGC
AAGGTCAACA AGAGCTATCC ATCCCTCACC ACCAAGGTGG AGGAGTCTGG CGAGCATGTG
ATCCTGGGCA CTGGGGAGCT CTACCTGGAC TGTGTGATGC ATGATTTGCG GAAGATGTAC
TCAGAGATAG ACATCAAGGT GGCTGACCCA GTTGTACGT TTTGTGAGAC GGTCGTGGAA
ACATCCTCCC TCAAGTGCTT TGCTGAAACG CCTAATAAGA GAACAAGAT CACCATGATT
GCTGAGCCTC TTGAGAAGGG CCTGGCAGAG GACATAGAGA ATGAGGTGGT CCAGATTACG
TGGAACAGGA AGAAGCTGGG AGAGTTCTTC CAGACCAAGT ACGATTGGGA TCTGCTGGCT
GCCCGTTCCA TCTGGGCTTT TGGCCCTGAT GCGACTGGCC CCAACATTCT GGTGGATGAT
ACTCTGCCCT CTGAGGTGGA CAAGGCTCTT CTTGGTTCAG TGAAGGACAG CATCGTTCAA
GGT
```

*Fig 1A*

```
TTGGGGACAT TTTGGGGTGA CACACTGAAC TGCTGGATGC TATCAGCATT TAGTAGGTAT
GCTCGATGTC TTGCAGAAGG ACATGATGGT CCTACACAGT AAGGAATGGA TTACCTACAA
TATTAATAGC AGCCTCCCAT ACACACTTTT GACACCCTTC CCTAAAGGAT TAATATGCTC
CAACCTTCCT GTCCCCACAG TTCAGTGGCT CTCCCTACCC TCACCATGAT CGGATGAAAA
AAAATAAGGT TTCACAGCTT AAGAGTGAAA TTCTGGAATC CAACTACAAG CTCATAACTG
TAGCATGGAA CCTGGTAGTA GCATAATAAA TAAATTTTTA GTAAGAGGCT TAAGAAATTT
TAGCAAAAAA AGCACTCCCT TTCTTCCTCC CTACATATCT CATATGTTTT TCAACACAAA
AAATTCTGTG ATTTTAGAGA AACTTCTTAC AGTACTTTTA AGTTCAAAAC CAGATGCTCA
TTACAGTTCT TTTAAACACC AAACTAGTCA TCTCAAAAAT ATGGCTAACT CTCTGGACTA
AATTCCATAG GAAAAATTAT TAATTTCAAA ATGCCTAATT TTTGATCAAT GCTGAAGAGC
CAAGCAATCA TGTCCTGCTT CTCACTCAGG GCAGAGTTCT CAGGTCAGAA GCTCCGGAGT
CTGTCAGAGA TTAAAATATC ATCTCAACAA TTCACAAGCT ACTTCTAAGT GTTACCCTAA
ATTAGTCACT AATCGTTTCT CCCCCAACTC TATTTCACAA ATTAAAGTTT ACAGAATTGA
CAAAAACCAA ACCAATGAAA CAACCCAGGC TATTTGCAGG GGGGGGGAAA GAGATACCCC
AAAAGTCAAC CCTATTTACA CGTAGTTAAA AGAGTGATCC AACAGATATT ACCCTCCATA
AAGTACCTAA AGGCAGGAGC CGGAATT
```

*Fig. 1B*

```
TTGGGGACAT TTTGGGGTGA CACACTGAAC TGCTGGATGC TATCAGCATT TAGTAGGTAT
GCTCGATGTC TTGCAGAAGG ACATGATGGT CCTACACAG
```

| GROUP | NUMBER | % SURVIVAL | |
|---|---|---|---|
| CONTROL | 7 | 44.6 ± 7.5 | (a) |
| 35kD (MNTF1) | 7 | 76.5 ± 10.8 | |
| 22kD (MNTF2) | 7 | 71.3 ± 8.7 | |
| 35kD + 22kD | 7 | 86.8 ± 5.8 | |

SURVIVAL VALUES ARE MEAN ± S.D.

% MOTONEURON SURVIVAL

| TREATMENT | 1 WEEK PO | (n) | 2 WEEKS PO | (n) |
|---|---|---|---|---|
| CONTROL | 53.4 ± 13.2 | (3) | 35.3 ± 9.2 | (a) |
| 35kD | 70.9 ± 10.4 | (4) | 57.1 ± 6.3 | (4)[a] |
| 22kD | 67.6 ± 10.4 | (5) | 56.3 ± 4.3 | (3)[a] |
| 35kD + 22kD | 64.2 ± 6.6 | (5) | 53.1 ± 0.4 | (3)[a] |

VALUES ARE MEAN ± S.D.

| TREATMENT | 1 WEEK PO | 2 WEEKS PO | SD (1 wk PO) | SD (2 wks PO) |
|---|---|---|---|---|
| CONTROL | 53.4 | 35.3 | 13.2 | 9.2 |
| 35kD (MNTF1) | 70.9 | 57.1 | 10.4 | 6.3 |
| 22kD (MNTF2) | 67.6 | 56.3 | 10.4 | 4.3 |
| 35kD + 22kD* | 64.2 | 53.1 | 6.6 | 0.4 |

% MOTONEURON SURVIVAL

| TREATMENT | 2 WEEK PO | (n) |
|---|---|---|
| 35kD + GOAT ANTI-RABBIT IgG | 80.1 ± 11.3 | (5)[b] |
| 22kD + ANTI-35kD MAb | 49.4 ± 0.9 | (5)[b] |

VALUES ARE MEAN ± S.D.

$p < 0.001$

ANTI-35kD Mab = MONOCLONAL ANTIBODY DIRECTED AGAINST 35 kD MOTONEURONOTROPHIC FACTOR.

*Fig. 11A*

POLYNUCLEOTIDES ENCODING MOTONEURONOTROPHIC FACTORS

CROSS-REFERENCE TO RELATED APPLICATIONS

This application is a continuation-in-part of U.S. patent application Ser. No. 08/751,225, entitled "Motoneuronotropic Factors," filed Nov. 15, 1996, now abandoned: which is a continuation in part of U.S. Provisional Application No. 60/026,792, entitled "Use of Motoneuronotropic Factors," filed on Sep. 27, 1996, now abandoned, which are hereby rated by reference.

FIELD OF INVENTION

The present invention relates to the human genes which encode a specialized group of proteins which promote the growth, maintenance, survival, and functional capabilities of selected populations of neurons.

BACKGROUND OF INVENTION

Neuronotrophic factors (NTFs) are a specialized group of proteins which function to promote the survival, growth, maintenance, and functional capabilities of selected populations of neurons. Recent studies have demonstrated that neuronal death occurs in the nervous systems of vertebrates during certain periods of growth and development. However, the addition of soluble neuronal trophic factors from associated target tissues serves to mitigate this phenomenon of neuronal death. The following citations discuss neuronal trophic factors and their disclosures are hereby incorporated by reference: Chau, R. M. W., et al., Neuronotrophic Factor, 6 *Chin. J Neuroanatomy* 129 (1990); Kuno, M., Target Dependence of Motoneuronal Survival: The Current Status, 9 *Neurosci. Res.* 155 (1990); Bard, Y. A., Trophic Factors and Neuronal Survival, 2 *Neuron* 1525 (1989); Oppenheim, R. W., The Neurotrophic Theory and Naturally Occurring Motoneuron Death, 12 *TINS* 252 (1989); Bard, Y. A., What, If Anything, is a Neurotrophic Factor?, 11 *TINS* 343 (1988); and Thoenen, H., and Edgar, D., Neurotrophic Factors, 229 *Science* 238 (1985).

In the vertebrate neuromuscular system, the survival of embryonic motoneurons have been found to be dependent upon specific trophic substances derived from the associated developing skeletal muscles. Skeletal muscles have been shown, by both in vivo and in vitro studies, to produce substances which are capable of enhancing the survival and development of motoneurons by preventing the embryonic motoneurons from degeneration and subsequent, natural cellular death. See O'Brian, R. J. and Fischbach, G. D., Isolation of Embryonic Chick Motoneurons and Their Survival In Vitro, 6 *J. Neurosci.* 3265 (1986); Hollyday, M. and Hamburger, V., Reduction of the Naturally Occurring Motor Neuron Loss by Enlargement of the Periphery, 170 *J. Comp. Neurol.* 311 (1976), whose disclosures are incorporated herein by reference. Similarly, several investigators have reported that chick and rat skeletal muscles possess certain trophic factors which can prevent the natural cellular death of embryonic motoneurons both in vivo and in vitro. See McManaman, J. L., et al., Purification of a Skeletal Muscle Polypeptide Which Stimulates Choline Acetyltransferase Activity in Cultured Spinal Cord Neurons, 263 *J.Biol. Chem.* 5890 (1988); Oppenheim, R. W., et al., Reduction of Naturally Occurring Motoneuron Death In Vitro by a Target Derived Neurotrophic Factor, 240 *Science* 919 (1988); and Smith, R. G., et al., Selective Effects of Skeletal Muscle Extract Fractions on Motoneurons Development In Vivo, 6 *J. Neurosci.* 439 (1986), whose disclosures are incorporated herein by reference.

In addition, a polypeptide has been isolated from rat skeletal muscle which has been found to selectively enhance the survival of embryonic chick motoneurons in vivo, as well the activity of choline acetyltransferase in these motoneurons. This polypeptide has been named Choline Acetyltransferase Development Factor (CDF) and its biological function has been demonstrated to be different from other trophic factors such as Nerve Growth Factor (NGF), Ciliary Ganglion Neurotrophic Factor (CNTF), Brain-Derived Neurotrophic Factor (BDNF), and Retinal Ganglion Neurotrophic Factor (RGNTF). See Levi-Montalcini, R., "Developmental Neurobiology and the Natural History of Nerve Growth Factor," 5 *Ann. Rev. Neurosci.* 341 (1982); Varon, S., et al., Growth Factors. In: *Advances in Neurology,* Vol. 47: Functional Recovery in Neurological Disease, Waxman, S. G. (ed.), Raven Press, New York, pp. 493–521 (1988); Barde, Y. A., Trophic Factors and Neuronal Survival, 2 *Neuron* 1525 (1989); Chau, R. M. W., et al., The Effect of a 30 kD Protein from Tectal Extract of Rat on Cultured Retinal Neurons, 34 *Science in China,* Series B, 908 (1991), whose disclosures are incorporated herein by reference.

The inventor of the invention disclosed in the instant application, Dr. Raymond Ming Wah Chau, presented results which reported the isolation and characterization of two motoneuronotrophic factors from rat muscle tissue having apparent molecular weights of 35 kD and 22 kD. This data was initially disseminated in 1991 at the World Congress of Cellular and Molecular Biology held in Paris, France. See Chau, R. M. W., et al., Muscle Neuronotrophic Factors Specific for Anterior Horn Motoneurons of Rat Spinal Cord. In: *Recent Advances in Cellular and Molecular Biology,* Vol. 5, Peeters Press, Leuven, Belgium, pp. 89–94 (1992), the disclosure of which is hereby incorporated by reference. This 35 kD protein has been defined by Dr. Chau as motoneuronotrophic factor 1 (MNTF 1) and the apparent 22 kD protein as motoneuronotrophic factor 2 (MNTF2). These two trophic factors have been demonstrated in vitro by Dr. Chau to support the growth and/or regeneration of both isolated anterior horn motoneurons and spinal explants of rat lumber spinal cord.

Subsequently, in 1993, Dr. Chau reported the successful cloning of human MNTF1, a protein having an apparent molecular weight of 55 kD, and its associated receptor from a human retinoblastoma cDNA library. See Chau, R. M. W., et al., Cloning of Genes for Muscle-Derived Motoneuronotrophic Factor 1 (MNTF1) and Its Receptor by Monoclonal Antibody Probes, (abstract) 19 *Soc. for Neurosci.* part 1, 252 (1993), the disclosure of which is hereby incorporated by reference. The cloned human MNTF1 was demonstrated to have biological activity similar to that of the "native" MNTF1 protein in that it supported the in vitro growth of rat anterior horn motoneurons.

Although various biological aspects of MNTF1 have been widely publicized in scientific journals, the DNA and inferred amino acid sequences of the cloned human MNTF1 gene and its associated receptor had not yet been made publicly available by Dr. Chau, nor had these sequences been confirmed by peer-review within the field. Moreover, the cloned human MNTF1, reported by Dr. Chau in 1993, was not in a form which was amenable to being sub-cloned into an appropriate vector, such as an in vitro mammalian expression system. Thus, there remained a need for the human MNTF1 gene to be properly manipulated, sequenced, sub-cloned into an appropriate vector(s), sub-cloned into an appropriate expression system(s) and associated host(s), as well as the isolation and purification of the resulting recombinant human MNTF1 protein for subsequent potential utilization in human therapeutic modalities.

SUMMARY OF THE INVENTION

The present invention is directed to a family of motoneuronotrophic factors including MNTF1 and MNTF2, which have been shown to have diagnostic and therapeutic applications in mammals. The present invention is also directed to novel DNA sequences which encode motoneuronotrophic factors, including recombinant human MNTF1-F3 [SEQ ID NO:1] and MNTF1-F6 [SEQ ID NO:2], to vectors which contain these novel DNA sequences, to expression systems and associated hosts which contain these novel DNA sequences, and the novel recombinant human MNTF1-F3 [SEQ ID NO:3] and MNTF1-F6 [SEQ ID NO:4] proteins which are produced by the aforementioned expression systems.

The present invention is also directed to the use of motoneuronotrophic factors for promoting axonal regeneration, for inhibiting the effects of hereditary motoneuron disease, for minimizing or inhibiting the effects of scar tissue formation, and for accelerating wound no healing while concomitantly minimizing or inhibiting the effects of scar tissue and keloid formation.

DESCRIPTION OF THE FIGURES

The present invention may be better understood and its advantages appreciated by those individuals skilled in the relevant art by referring to the accompanying figures wherein:

FIG. 1A depicts the DNA sequence of the MNTF1-1443 DNA fragment [SEQ ID NO:1] which encodes the MNTF1-F3 protein. By standard convention, the DNA sequence is shown in the 5' to 3' directed.

FIG. 1B depicts the DNA sequence of the MNTF1-927 DNA fragment [SEQ ID NO:2] which encodes the MNTF1-F6 protein. The first 99 of these nucleotides [SEQ ID NO:5] correspond to and code for the 33 amino acid peptide shown in FIG. 2B. By standard convention, the DNA sequence is shown in a 5' to 3' orientation.

FIG. 1C depicts the first 99 nucleotides [SEQ ID NO:5] (33 codons) of the DNA sequence shown in FIG. 1B.

FIG. 2A depicts the direct amino acid sequence of MNTF1-F3 protein [SEQ ID NO:3]. By standard convention, the amino acid sequence is reported from the amino (NH2-) terminus to the carboxyl (—COOH) terminus.

FIG. 2B depicts the direct amino acid sequence of MNTF1-F6 protein [SEQ ID NO:4] encoded by the MNTF1-927 DNA fragment. By standard convention, the amino acid sequence is reported from the amino (NH2-) terminus to the carboxyl (—COOH) terminus.

FIG. 3 (panels a–c) illustrate the results obtained utilizing the "Protein Band-Fishing By Cells" methodology to isolate the motoneuronotrophic factors MNTF1 and MNTF2.

FIGS. 8A and 8B provide histogram and tabular results of the synergistic protection and rescue of axotomized motoneurons of the sciatic nerve by the partially-purified and isolated motoneuronotrophic factors MNTF1 and MNTF2 following the transection of the sciatic nerve in Sprague Dawley rats.

FIGS. 10A and 10B provide histogram and tabular results of the in vivo effects of muscle-derived motoneuronotrophic factors (22 kD, 35 kD, and 22 kD+35 kD) on neuronal survival following the transection of the facial nerve in Sprague Dawley rats.

FIGS. 11A and 11B provide histogram and tabular results of the in vivo effects of muscle-derived 35 kD MNTF1 motoneuronotrophic factor on neuronal survival following the transection of the facial nerve in Sprague Dawley rats in the presence of goat anti-rabbit IgG or anti-35 kD motoneuronotrophic factor monoclonal antibody.

FIG. 20A reveals nerve fibers; one~1.5 mm and the other 3 mm were regenerated from the cultured motoneurons. Low magnification (×40). FIG. 20B is a high magnification (×140) of FIG. 20A and a composite picture to reveal the myelinated, regenerated nerve fiber with oligodendrocytes (possible Schwann cells?*) attached. FIGS. 20C and 20D reveal clearly the axon cylinders in the inner regenerated myelinated nerve fiber with node of Rannier. High magnification (×400).

DESCRIPTION OF THE INVENTION

Figures 3A, 3B, 3C:
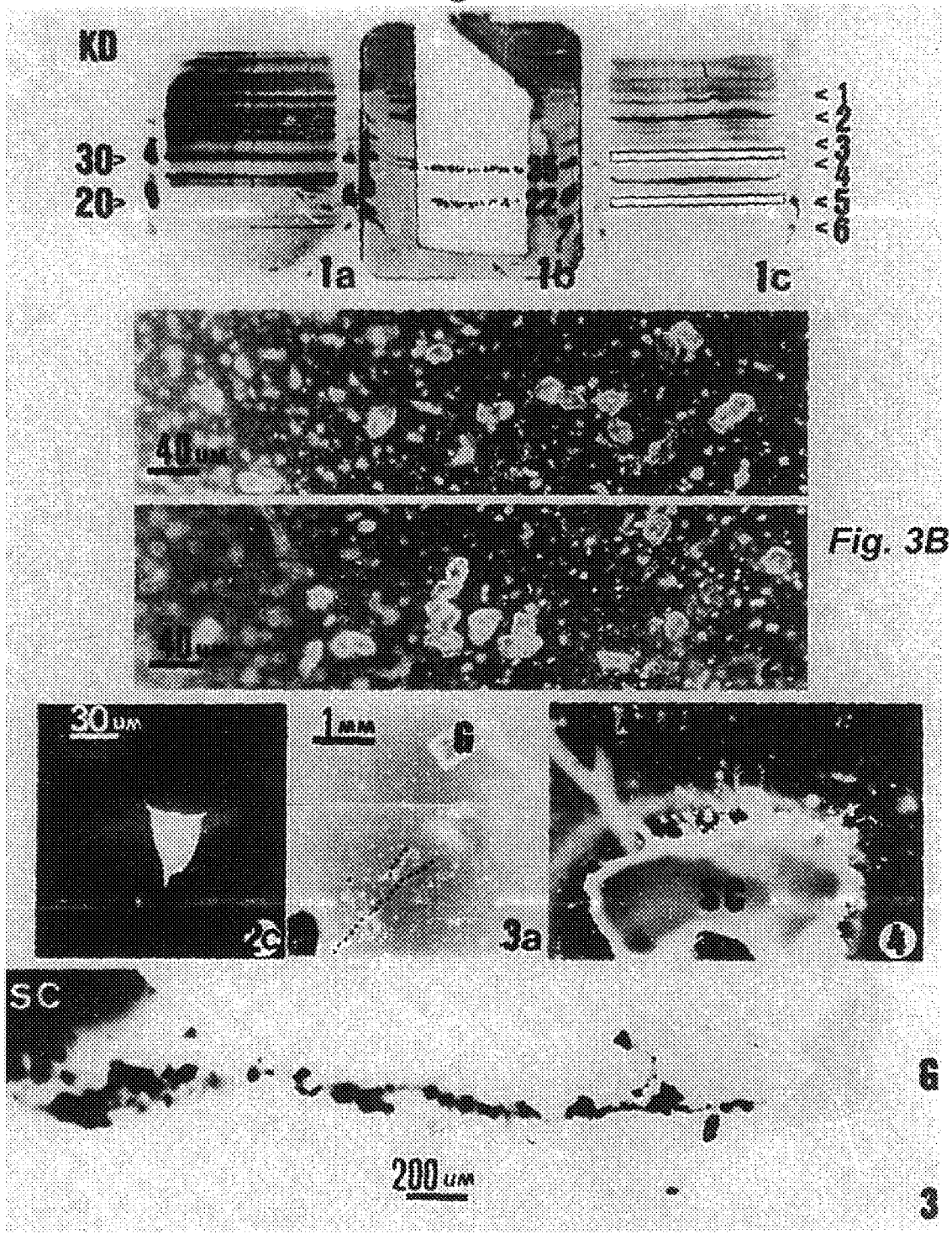
FIG. 3 (panels A–C) depicts the "Protein Band-Fishing By Cells" methodology which showed that isolated anterior horn motoneurons survived and grew on PhastGel regions containing MNTF1 and MNTF2 from muscle extract which had been electrophoretically separated into protein bands within the PhastGel.

The present invention comprises a family of neuronotrophic factors which possess the ability to exert a trophic effect on motoneurons and the genes which encode these factors. These factors have been isolated and the genes which encode these factors have been cloned and expressed, and both the nucleic acid and polypeptide sequences provided.

It has been demonstrated that the isolated factors and the expressed, recombinant factors are capable of inducing the continued viability and neurite outgrowth of motoneurons. Therefore, these factors have been classified as "motoneuronotrophic factors" or "MNTFs."

MNTFs have been isolated from both rat and human sources and their biological activities have been examined both in vivo and in vitro. For example, their potential biological activity has been examined in both surgically-axotomized and hereditarily diseased animals.

The MNTFs disclosed in the present invention are useful for a variety of purposes. They can be utilized in the diagnosis of motoneuron diseases by exploiting their effectiveness in altering the symptomology of the disease. For example, a detailed description is provided below which supplies evidence of the successful use of MNTF1-F3 and MNTF1-F6 in wobbler mice. Wobbler mice are animals which possess double recessive genes for a hereditary motoneuron disease. The motoneuron disease manifests itself with symptoms of upper limb neuromuscular failure which initially appears approximately 3 weeks after birth. The condition also affects the animal's body weight, general health conditions, respiration, and life span in a deleterious manner. The disease gradually progresses to the final, terminal stage (defined as stage 4) by 3 months of age, with an associated dramatic increase in animal mortality. The symptomatic responsiveness of the wobbler mice to the aforementioned MNTFs is indicative of the defect occurring at the motoneuron level, thus serving to confirm various genetic evidence which has established the hereditary nature of the defect.

In addition, MNTFs may also be utilized therapeutically to treat damaged or diseased motoneurons. For example, a detailed description is provided below which includes experiments using these factors on surgically-transected motoneurons, with the resulting recovery of a large percentage of the transected motoneurons. Also described is the utilization of the factors in the aforementioned hereditary motoneuron disease, the wobbler mouse, with results demonstrating that the treated animals survived, with a concomitant arresting of pathological symptomologies, and thrived for much longer periods of time than those of the untreated animals.

"Protein Band-fishing by Cells" Methodology

Rat MNTF1 and MNTF2 were isolated utilizing the "Protein Band-Fishing by Cells" methodology as reported in Chau, R. M. W., et al., Muscle Neuronotrophic Factors Specific for Anterior Horn Motoneurons of Rat Spinal Cord. In: *Recent Advances in Cellular and Molecular Biology*, Vol. 5, Peeters Press, Leuven, Belgium, pp. 89–94 (1992). Trophic factors are generally found in minute quantities in vivo; hence this can potentially cause tremendous difficulties in their isolation utilizing traditional biochemical methodologies. In view of this fact, a novel technique designated "Protein Band-Fishing by Cells" was developed in which viable anterior horn motoneurons were co-cultured on an electrophoretic gel containing the separated proteins from rat peroneal muscle. This methodology thus allowed the viable anterior horn motoneurons to "fish-out" those peroneal muscle proteins which exhibited biological activity specific for those motoneurons (i.e., by the demonstration of continued viability and growth in vitro).

For electrophoretic protein separation, the peroneal longus and brevis skeletal muscles, without the associated tendon, from 3 week-old Sprague Dawley rats were aseptically dissected into small sections and washed 3-times in $Ca^{+2}/Mg^{+2}$-free Hank's medium. The muscle tissue was then homogenized in 10 mM Tris-HCl (pH 7.2). A cell lysate was obtained by centrifugation at 100,000×g. for 10 minutes, and the supernatant was filtered utilizing a 0.2 m Millipore filter membrane (Millipore Corp., Mass.). The resultant filtrate was designated muscle extract (Me).

For cell culture, the spinal cords from four 3 week-old rats were excised and the meninges and any associated vessels were removed. It should be noted that the motoneurons were pre-labeled with rhodamine B for subsequent microscopic visualization by implantation of gelfoams containing rhodamine B into the peroneal muscles of the experimental animals one week prior to their sacrifice. The gray matter of the anterior horn region of segments L4–L5 was subsequently removed from each excised spinal cord, washed several times in $Ca^{+2}/Mg^{+2}$-free medium, and treated with collagenase (0.08%) at 37° C. for 60 minutes. Following gentle dissociation and sedimentation, the cell were suspended in RPMI 1640 medium/6% fetal calf serum/20 mM HEPES/1x streptomycin and penicillin and utilized for subsequent PhastGel culture.

The filtered, muscle extract (Me, 10–20 l of a 1 mg/ml solution) was then applied to a pre-cast 20% native PhastGel (50×40×0.45 mm, Pharmacia LKB Biotech AB, Upsala, Sweden) for separation by the Phast System gel electrophoresis (Pharmacia LKB Biotech AB, Upsala, Sweden). The electrophoretic conditions utilized were those suggested by the computer program of Olsson, I., et al., Computer Program for Optimizing Electrophoretic Protein Separation, 9 *Electrophoresis* 16 (1988).

Following electrophoresis, the middle portion of the PhastGel was removed via aseptic technique for subsequent culture with $\sim \times 10^6$ spinal cord cells/gel. The remaining portions of the PhastGel were stained using the silver stain method to identify and locate the resulting protein bands. Following 2–7 days of incubation, the PhastGel/spinal cell culture was fixed in 0.4% paraformaldehyde in Phosphate-buffered saline (PBS) for approximately 2 hours. This portion of the gel was then reinserted back into its original position of the PhastGel and examined for viable, large (~25 μm) rhodamine B retrograde-prelabeled motoneurons in the cultured spinal cells using either an inverted phase (Zeiss Axiophot Inverted Microscope, West Germany) or a fluorescent microscope (Zeiss, West Germany).

Silver staining demonstrated a total of 34 native protein bands (26 protein bands with an apparent molecular weight of >30 kD and 8 protein bands with an apparent molecular weight of <30 kD) separated from the muscle extract. These results are illustrated in FIG. 3, panels A–C. Interestingly, large (~25 μm) rhodamine B retrograde-prelabeled motoneurons from the cultured spinal cells were found to survive in only two spatially-distinct regions corresponding to the 35 kD and 22 kD apparent molecular weight protein bands. These results are demonstrated in FIG. 3, panel B. Moreover, silver staining methodology demonstrated heavier staining of the 35 kD protein band, in comparison to the 22 kD protein band, thus potentially reflecting the relative concentrations of these two trophic factors in the muscle extract. No other types of neuronal cells were found to have survived, nor did the aforementioned motoneurons remain viable in any other locations corresponding to additional proteins with differing apparent molecular weights. These aforementioned results are indicative of the large, rhodamine B retrograde-prelabeled motoneurons having "fished out," from the amongst the 34 total peroneal muscle protein bands, their own trophic factors having apparent molecular weights of 35 kD and 22 kD, and are illustrated in FIG. 3, panel C. The 35 kD and 22 kD protein bands were designated MNTF1 and MNTF2, respectively.

Determination of MNTF1 and MNTF 2 Biological Activity

The rat MNTF1 and MNTF2 proteins were then tested for potential biological activity with anterior horn motoneurons. Anterior horn motoneurons were isolated from four 3 week-old Sprague Dawley rat lumbar spinal cord via collection of the associated gray matter. The collected gray matter was then digested with a 0.08% collagenase solution in DMEM medium. The motoneurons in the DMEM medium were collected in 5 ml aliquots and allowed to settle at room temperature for 2 minutes. The upper 4.5 ml of supernatant was aspirated and discarded and the remaining media, containing the motoneurons, were subsequently utilized to test the biological activity of the rat MNTF1 and MNTF2 proteins.

Rat MNTF1 and MNTF2 were isolated utilizing the aforementioned Phast System gel electrophoresis apparatus by aseptic excision of the PhastGel sections (~1×30 mm) containing the 35 kD and 22 kD protein bands, respectively (see FIG. 3, panels A–C). Anterior horn motoneurons, isolated from the lumbar spine of 3 week-old Sprague Dawley rats, were then co-cultured with and without the presence of MNTF1- and MNTF2-containing PhastGel sections. Results indicated that both MNTF1- and MNTF2-containing PhastGel sections were capable of supporting the continued viability of the anterior horn motoneurons, as well as supporting neurite outgrowth.

Figure 4:
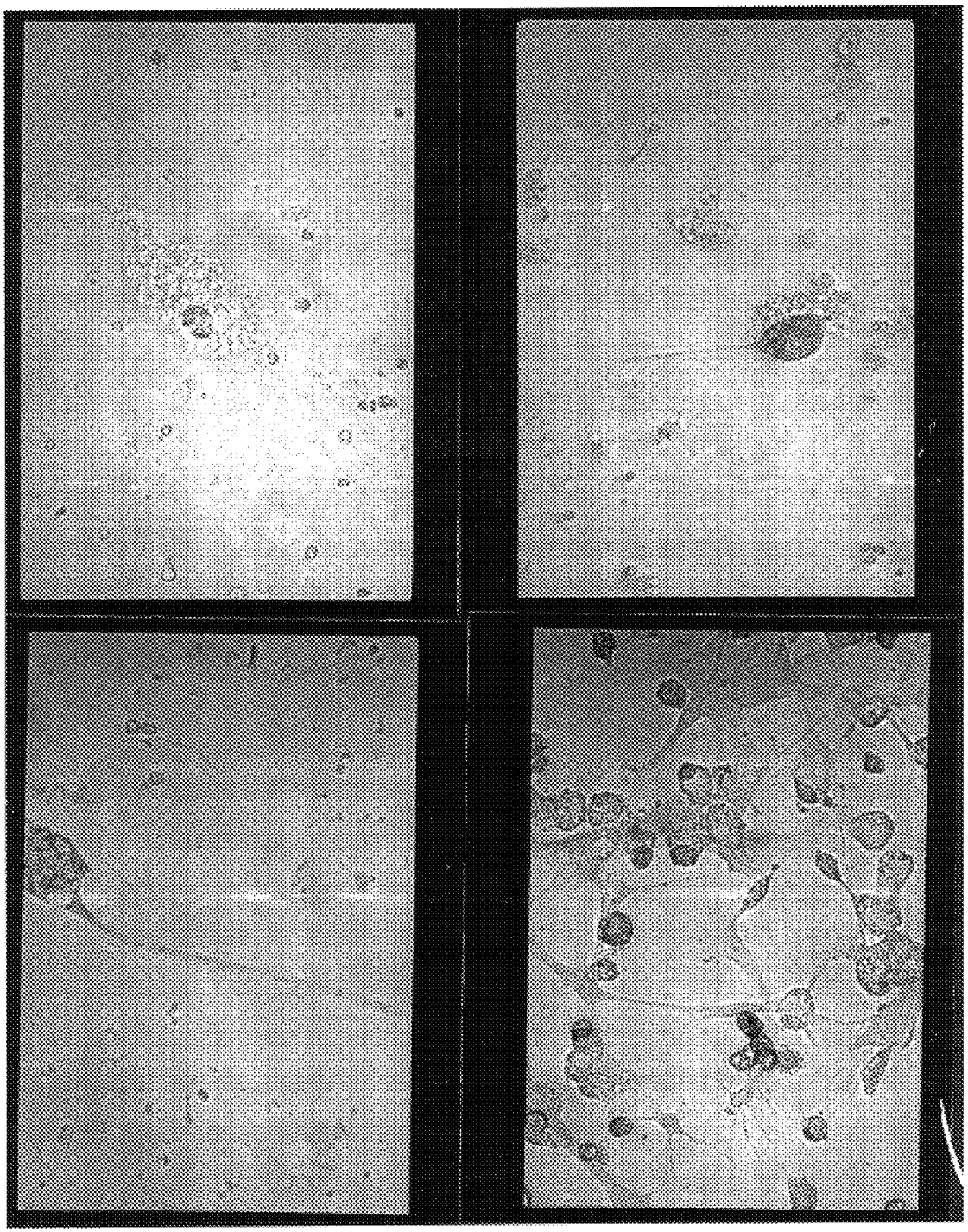
FIG. 4 (panels 1–4) reveals the results of isolated motoneurons cultured with the 35 kD gel band containing the MNTF1 for 3, 7, and 14 days (panels 2, 3, & 4, respectively) and a control culture (panel 1) without the 35 kD MNTF1-containing gel.

In a similar experiment, depicted in FIG. 4, panels 1–4, anterior horn motoneurons, isolated from the lumbar spine of 3 week-old Sprague Dawley rats, were then co-cultured with and without the presence of MNTF1-containing PhastGel sections for 3, 7, and 14 days (panels 2, 3, & 4, respectively). The results of this experiment are shown in FIG. 4 which demonstrates that MNTF1 is capable of supporting the continued viability of anterior horn motoneurons for 2 or more weeks. The determination of motoneuron viability and neurite outgrowth was performed utilizing both MTT micro-assay and microscopic morphological measurement. MTT is a highly sensitive, calorimetric tetrazolium derivative [3-(4,5-dimethylthiazol-2-yl)-2,5-dipheny tetrazolium bromide] which can be converted by viable cells to form a formazan product which can subsequently be measured with an ELISA colorimeter. The control assay (panel 1), utilizing selected remaining protein-containing PhastGel sections or PhastGel sections alone, failed to support any continued viability or neurite outgrowth of the anterior horn motoneurons.

Figure 6:
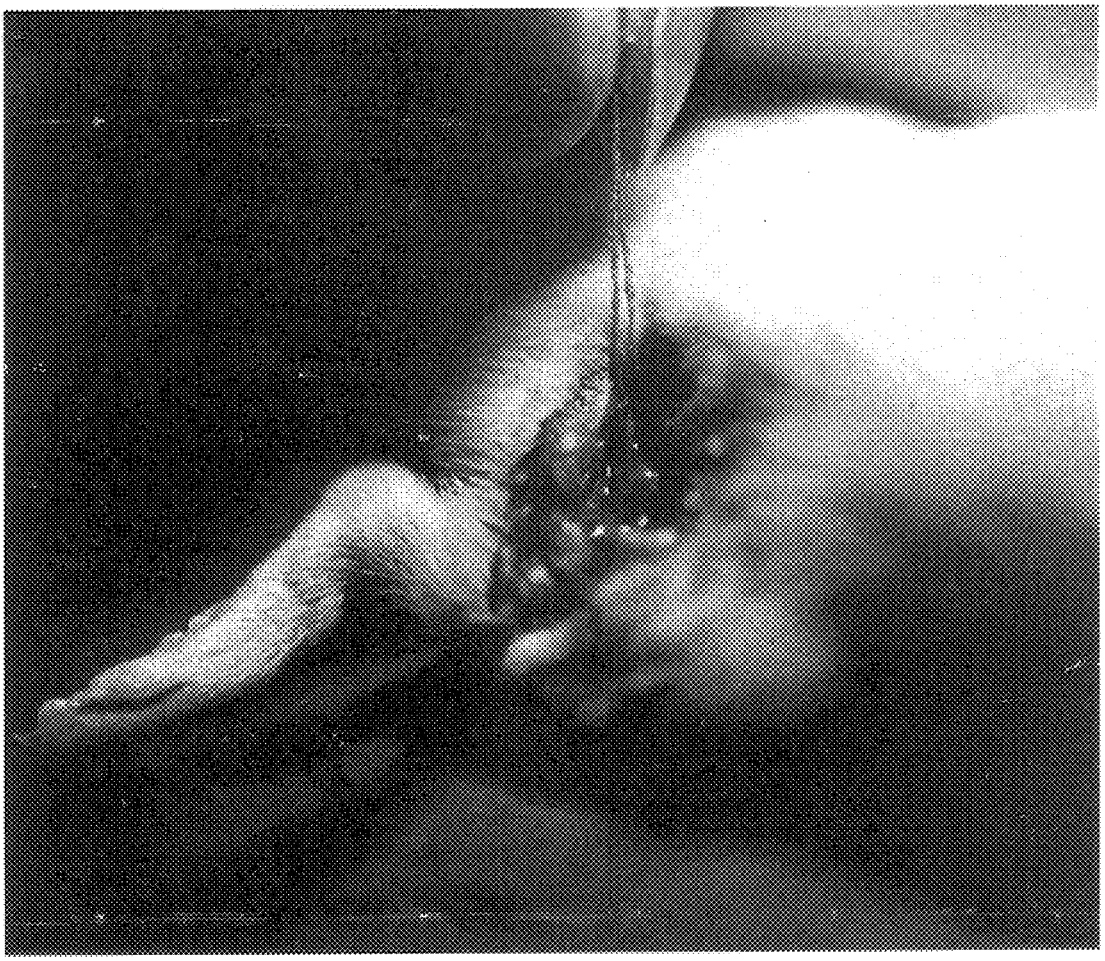
FIG. 6 depicts the axotomy of the sciatic nerve of a 10 day-old Sprague Dawley rat. The sciatic nerve at the gluteal region of the right side was axotomized with 1 mm of the nerve removed and MNTFs were subsequently placed around the cut edge of the nerve.

In Vivo Testing of Rat MNTF1 and MNTF2 in Axotomized Animals In vivo testing of rat MNTF1 and MNTF2 were next performed utilizing axotomized animals. Axotomized rat sciatic, facial, hypoglossal, and musculocutaneous nerves were cut in the right side of 10 day-old Sprague Dawley rats. The aforementioned nerves were left intact on the left side of the rats to serve as contralateral internal controls. Sections of MNTF1 and/or MNTF2-containing PhastGel (~2×3 mm sections containing 5–30 ng of MNTFs) were applied via implantation to the axotomized sites. The axotomy of the sciatic nerve and subsequent implantation of MNTF-containing gels(s) are illustrated in FIG. 6. In the surgical procedure, the right-side of the gluteal region was dissected so as to reveal the sciatic nerve. A 1 mm section of the sciatic nerve was resected and the remaining ends of the nerve were spatially aligned without performing an end-to-end anastomosis. The MNTF-containing and control gel sections were then placed around the surgical resection site and the initial incision was closed. Axotomized animals in which PhastGel without MNTFs were implanted in an analogous manner and were utilized as controls. After periods of 2, 4, and 8 weeks, the axotomized animals were sacrificed and tissue sections were excised and prepared for determination of motoneuron survival/viability via microscopic examination.

The results demonstrated that without the application of the MNTFs, 60–70% of the motoneurons associated with the aforementioned nerves had degenerated, therefore only 30–40% of the motoneurons were still viable at the time of microscopic examination. Conversely, in the presence of either MNTF1 or MNTF2, 55–75% of the motoneurons displayed continued viability during the above periods of observation. In the presence of both MNTF1 and MNTF2, 90% of the motoneurons were found to exhibit continued viability.

FIGS. 7 and 8 depict the results of the in vivo effects of muscle-derived motoneuronotrophic factors on neuronal survival following the transection of the sciatic nerve. As previously discussed, the sciatic nerves were cut in the right side of 10 day-old Sprague Dawley rats (see FIG. 6); whereas the sciatic nerves were left intact on the left side of the rats to serve as contralateral internal controls. Section of MNTF1-containing and/or MNTF2-containing PhastGel (~2×3 mm section containing 5–30 ng of MNTFs) were applied via implantation to the axotomized sites. MNTF1 and MNTF2 correspond to the 35 kD and 22 kD proteins, respectively. PhastGel sections without MNTFs were implanted in axotomized animals in an analogous manner, and served as controls. After 3 weeks, the axotomized animals were sacrificed and sections of the lumbar spinal cord were excised and prepared for determination of motoneuron survival/viability via microscopic examination. Results demonstrated that without the application of the MNTFs, 56% of the motoneurons associated with the aforementioned nerves had degenerated. Therefore, only 44% of the motoneurons were still viable at the time of microscopic examination. Conversely, in the presence of either the 35 kD protein MNTF1 or the 22 kD protein MNTF2, 76% and 71% of the motoneurons displayed continued viability, respectively, at the time of microscopic evaluation.

Figure 7A:
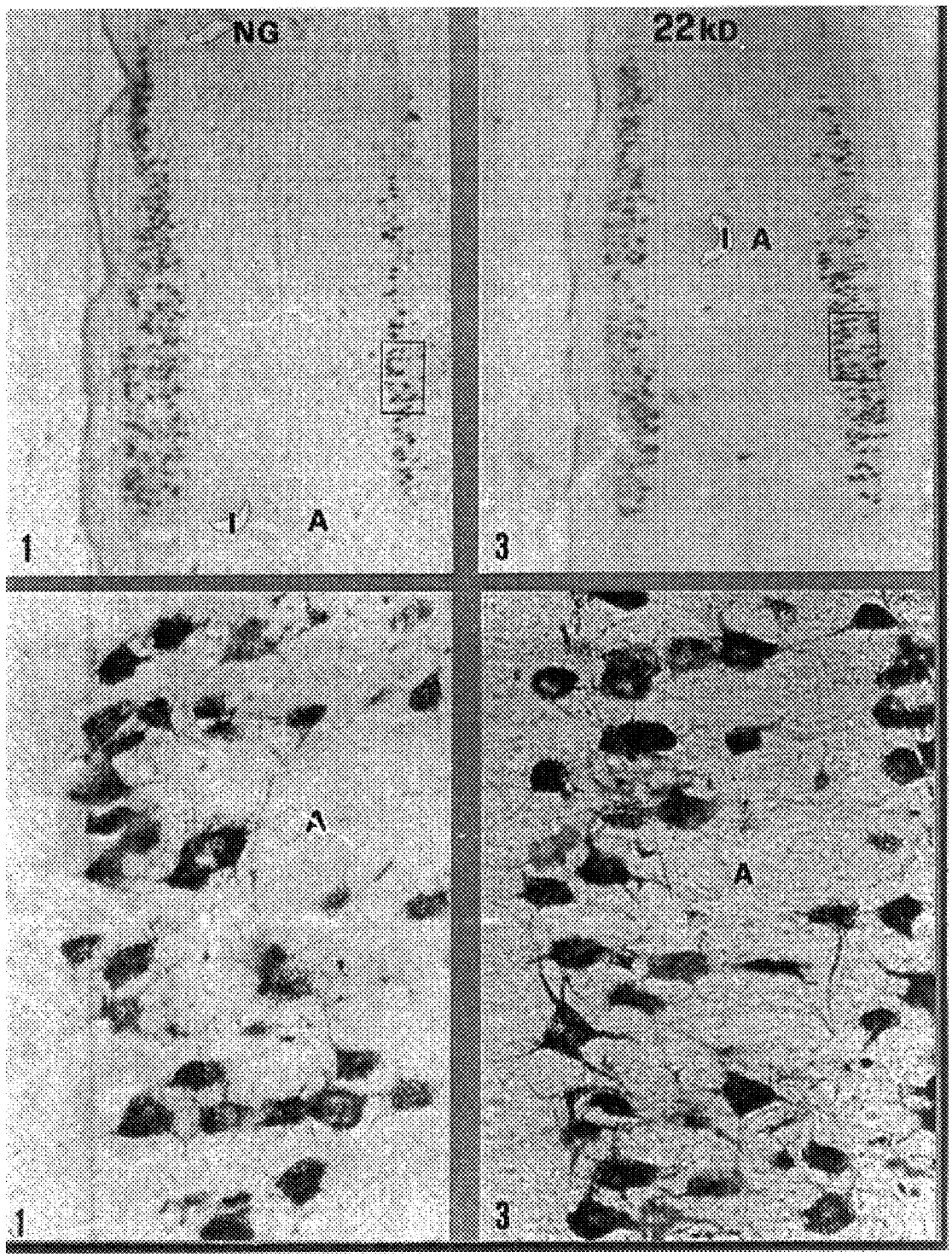
FIGS. 7A (panels 1 and 3) and 7B (panels 2 and 4) reveal the synergistic effect of MNTF1 (35 kD) and MNTF2 (22 kD) on the survival of axotomized motoneurons of the sciatic nerve in the Sprague Dawley rats. Panel 1 had no gel added (NG) and panel 3 had 22 kD MNTF2 gel added; (I) is the intact side and (A) is the axotomized side. Panel 2 had the 35 kD MNTF1 gel added and panel 4 had both the 35 kD and 22 kD gels added.
Figure 7B:
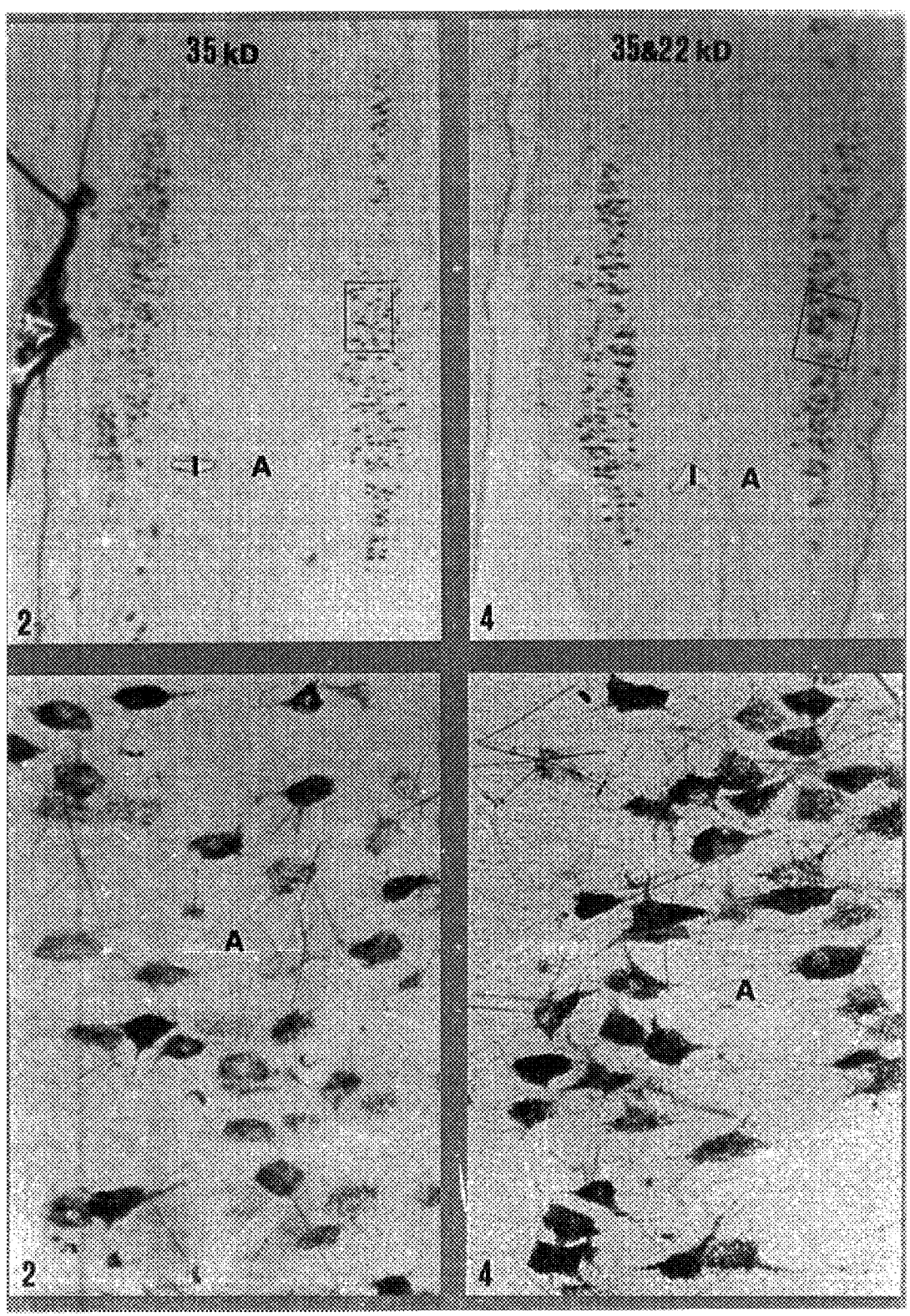
Figure 8B:
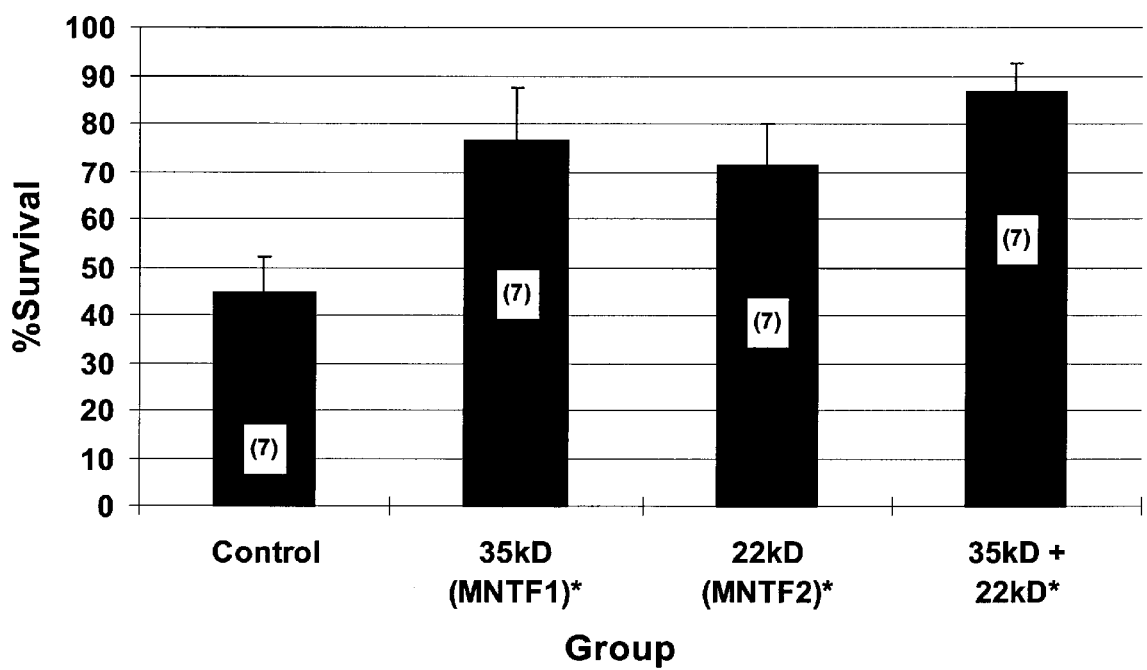

FIGS. 7A and 7B represents a series of eight photomicrographs depicting the in vivo effects of muscle-derived motoneuronotrophic factor on neuronal survival following transection of the sciatic nerve in Sprague Dawley rats. These results are presented in tabular and histogram form in FIG. 8A and 8B, respectively. In this series of experiments, axotomized sciatic nerves were cut in the right side of adult Sprague Dawley rats, whereas the left side sciatic nerve was left intact as an internal contralateral control. Sections of MNTF1-containing or MNTF2-containing PhastGel (~2×3 mm section containing 5–30 ng of MNTFs) were applied via implantation to the axotomized sites. PhastGel sections without MNTFs were implanted in axotomized animals in an analogous manner, and served as controls. It should be noted that all the lumbar 4 and 5 anterior horn motoneurons were retrogradely prelabeled with horseradish peroxidase (HRP) for 2 weeks prior to animal sacrifice, at which time sections of the sciatic nerve were excised and prepared for subsequent determination of motoneuron survival/viability via a microscopic cell counting methodology.

Results shown within the control photomicrographs (see FIG. 7A, panel 1) demonstrated that without the application of the MNTFs (NG), a comparatively low number of viable (i.e., HRP-labeled) motoneurons are present in all the serial sections of the axotomized side (A) of the lumbar spinal cord as compared to the intact side. This finding is corroborated by the tabular results presented in FIG. 8 which show that 56% of the HRP-labeled motoneurons associated with the sciatic nerve had degenerated. Conversely, in the presence of the 22 kD protein MNTF2 (see FIG. 7A, panel 3), the 35 kD protein MNTF1 (see FIG. 7B, panel 2), or both the 22 kD and 35 kD MNTFs (see FIG. 7B, panel 4) a markedly higher rate of survival of the HRP-labeled motoneurons was demonstrated. These results are quantitatively depicted in FIGS. 8A and 8B, and are corroborated by the fact that the utilization of the 35 kD MNTF1 protein or the 22 kD MNTF2 protein resulted in 76.5% and 71.3% of the HRP-labeled motoneurons displaying continued viability, respectively. Similarly, in the presence of both MNTF1 and MNTF2 (see FIG. 7B, panel 4), a large number of viable motoneurons are found with 86.8% of the motoneurons exhibiting continued viability as a result of treatment with both MNTFs (see FIGS. 8A and 8B).

Figure 9:
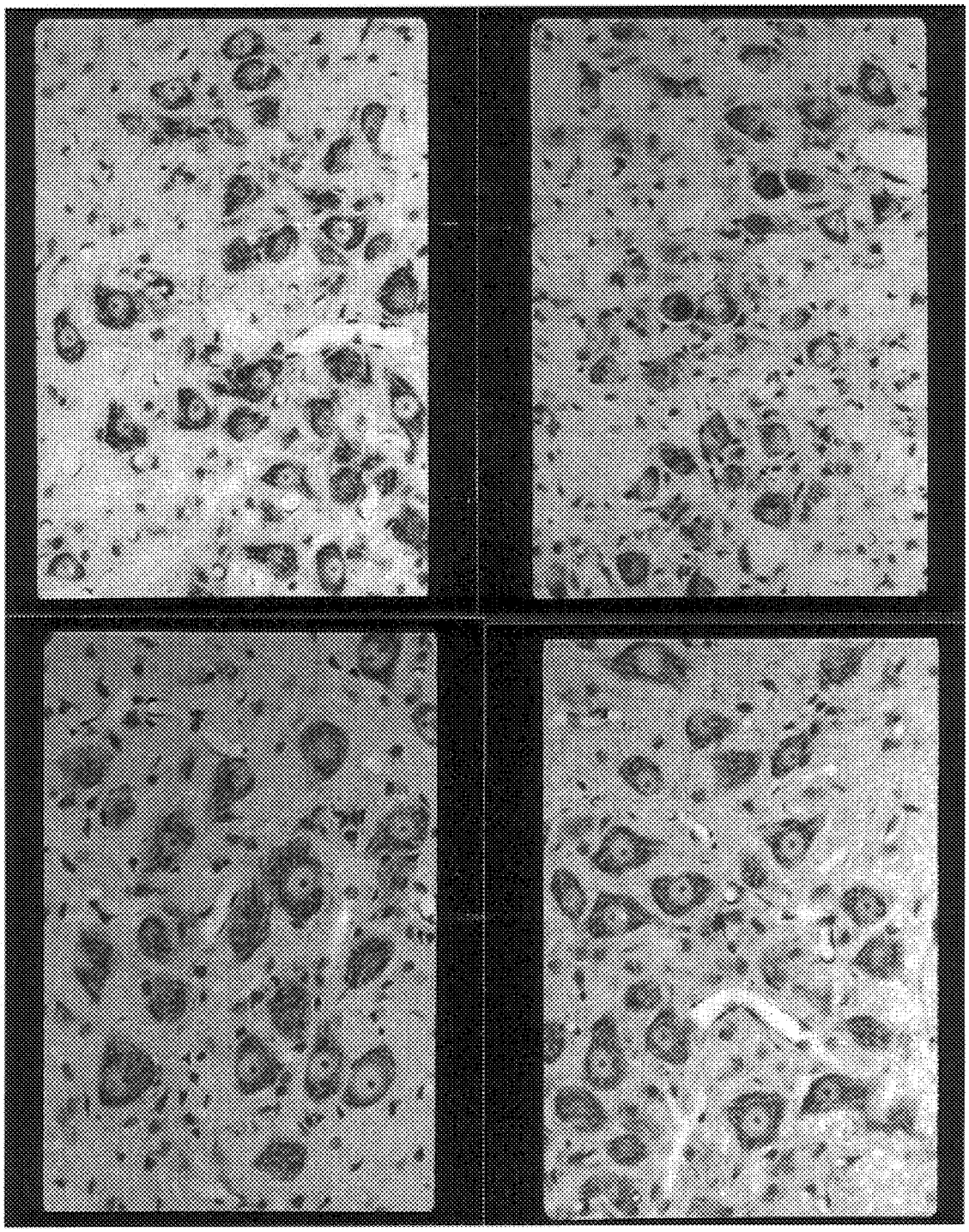
FIG. 9 (panels 1–4) reveals the microscopic effects of MNTFs on the survival of motoneurons in the facial nuclei of the transected facial nerve in the Sprague Dawley rats. Panel (1) the facial nuclei of the normal intact control rat after two weeks; panel (2) the axotomized facial nuclei without factors after two weeks; panels (3) and (4) the axotomized facial nuclei with 35 kD MNTF1 and with both 35 kD and 22 kD MNTF1 & MNTF2, respectively, for two weeks.
Figure 10B:
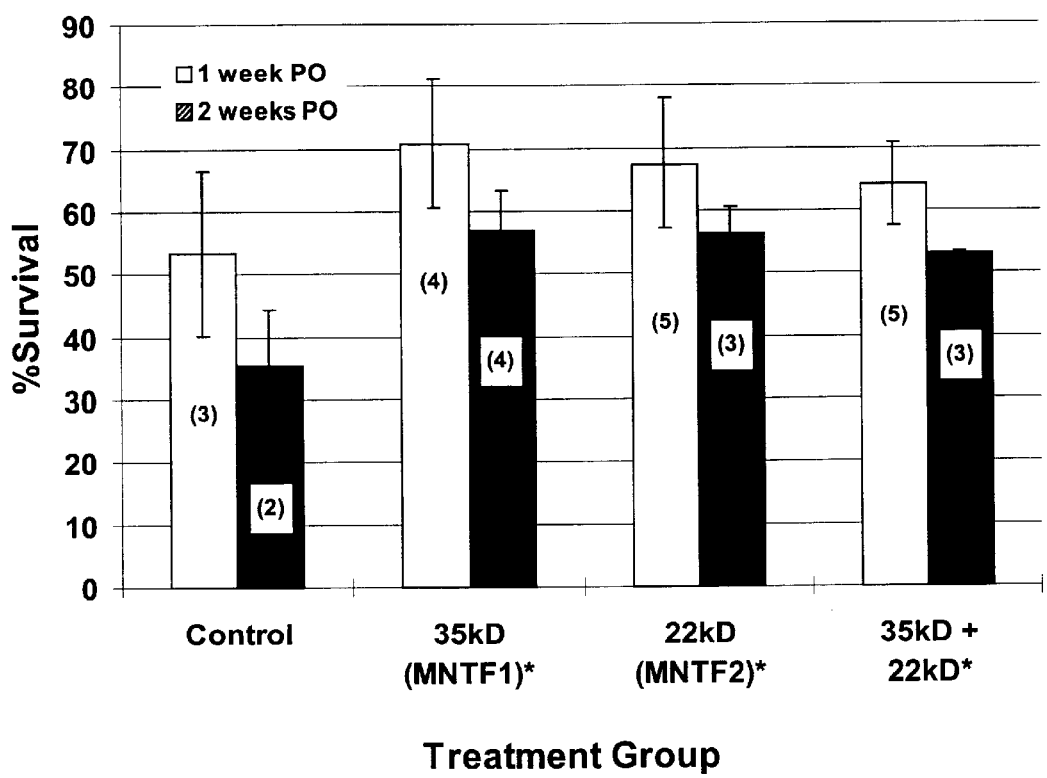

FIG. 9, panels 1–4 illustrates the results of the in vivo effects of MNTF application on neuronal survival and viability following the transection of the rat facial nerve in photomicrographic form. In this series of experiments, axotomized facial nerves were cut in the right side of 10 day-old Sprague Dawley rats, whereas the left-side facial nerves were left intact to serve as an internal contralateral control. Sections of MNTF1-containing or MNTF2-containing PhastGel (~2×3 mm section containing 5–30 ng of MNTFs) were applied via surgical implantation to the axotomized sites. As before, the MNTF1 and MNTF2 correspond to the 35 kD and 22 kD proteins, respectively. PhastGel sections without MNTFs were implanted in axotomized animals in an analogous manner, and served as controls. After periods of 1 and 2 weeks, the axotomized animals were sacrificed and serial sections of the facial nuclei in the brain were prepared for subsequent evaluation of motoneuron survival/viability via microscopic examination following histological staining. Results in FIG. 9, panel 1 depicts the facial nuclei of the normal intact control rat after two weeks; panel 2 depicts the axotomized facial nuclei without factors after two weeks; panels 3 and 4 depict the axotomized facial nuclei with 35 kD MNTF1 and with both 35 kD and 22 kD MNTF1 & MNTF2, respectively, after two weeks. FIGS. 10A and 10B illustrate the results in tabular and histogram form, respectively. The results shown in FIGS. 9, 10A and 10B demonstrated that without the application of either the MNTFs, ~50% of the motoneurons associated with the facial nuclei had degenerated after only one week and ~65% had degenerated after two weeks (panel 1). In contrast, in the presence of either the 35 kD protein MNTF1 (panel 3) or the 22 kD protein MNTF2 (panel 2), 70% of the motoneurons displayed continued viability after 1 week and 55% were still viable after 2 weeks. Similar results were obtained when both the 35 kD (MNTF1) and 22 kD (MNTF2) proteins were utilized (panel 4).

Figure 11B:
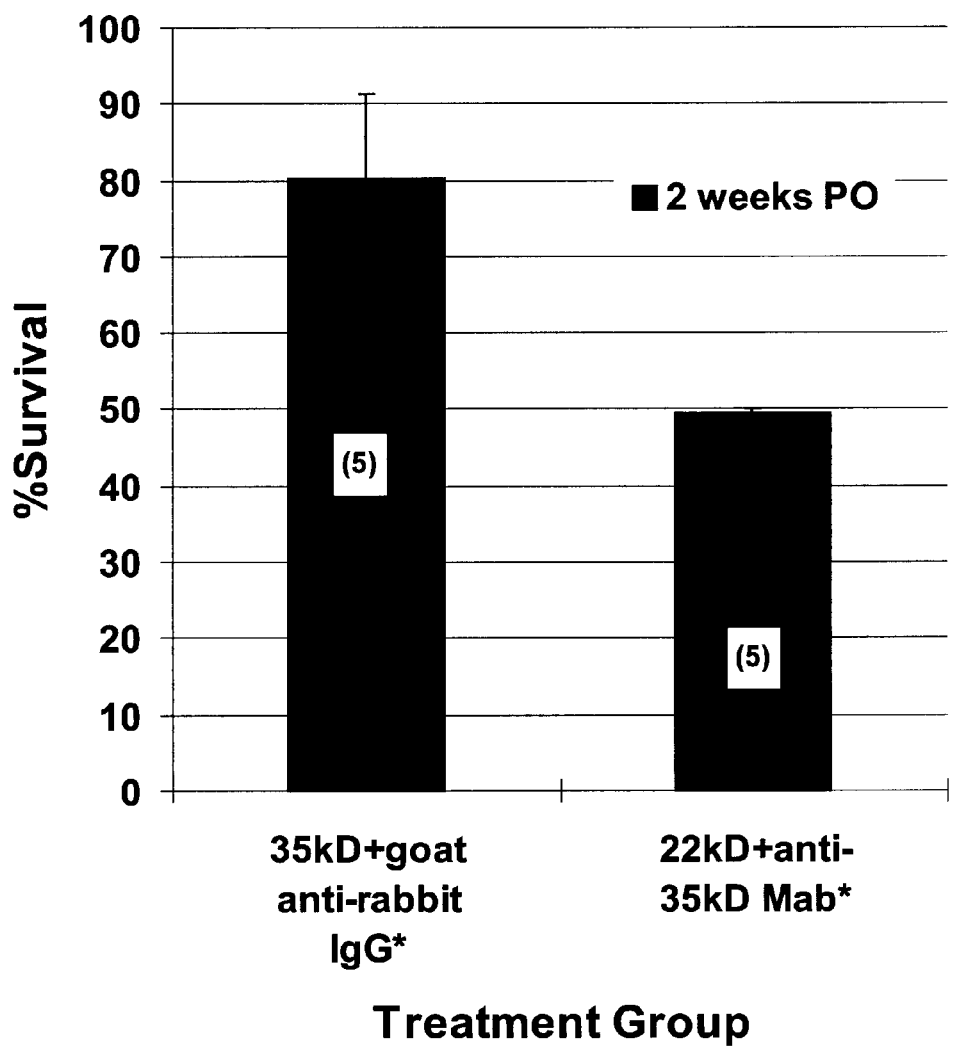
Figure 12A:
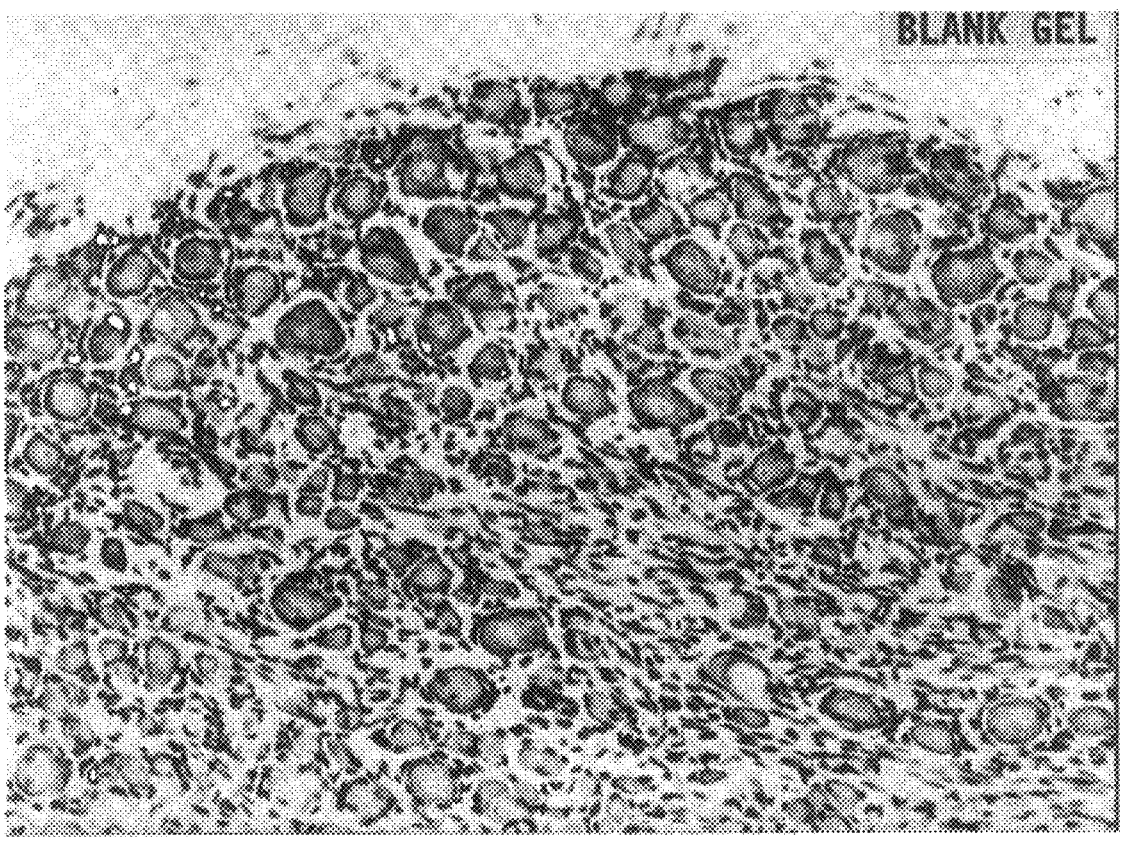
FIGS. 12A–D depicts a series of four photomicrographs demonstrating the in vivo effects of the 35 kD MNTF1 and 22 kD MNTF2 proteins upon neuronal survival following the transection of dorsal root ganglion in Sprague Dawley rats.
Figure 12B:
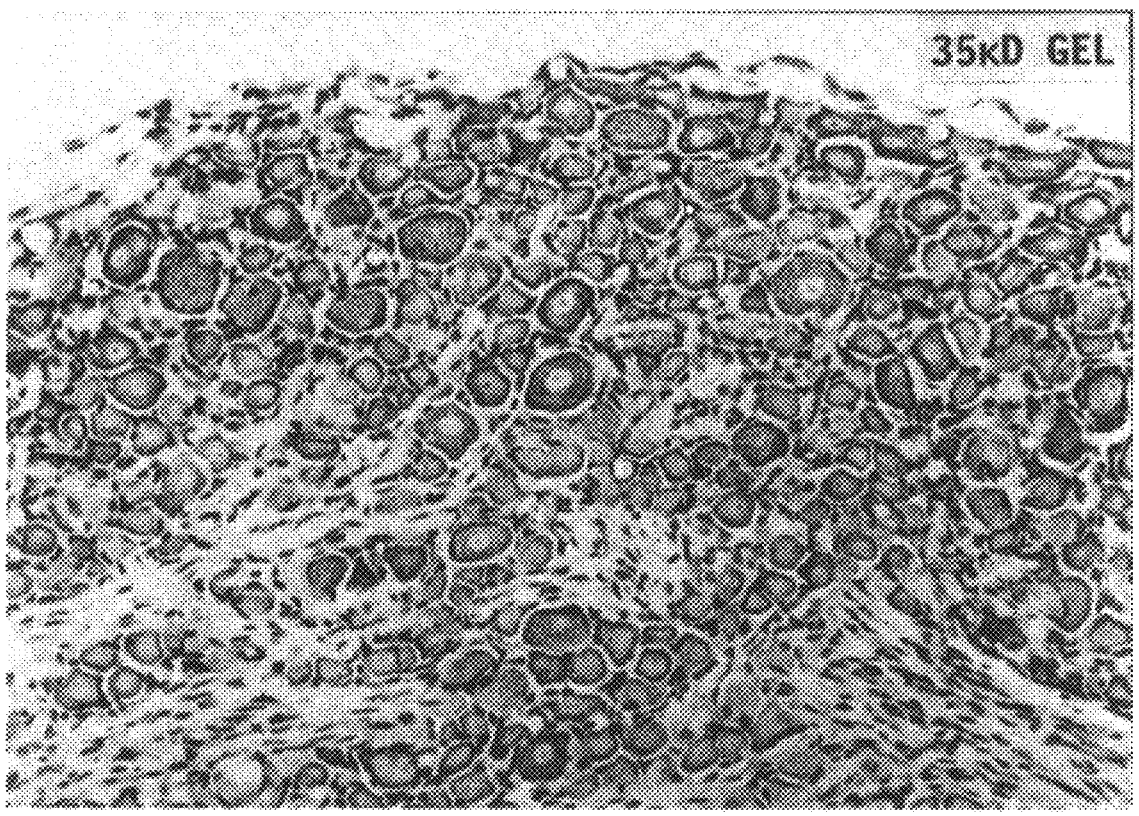
Figure 12C:
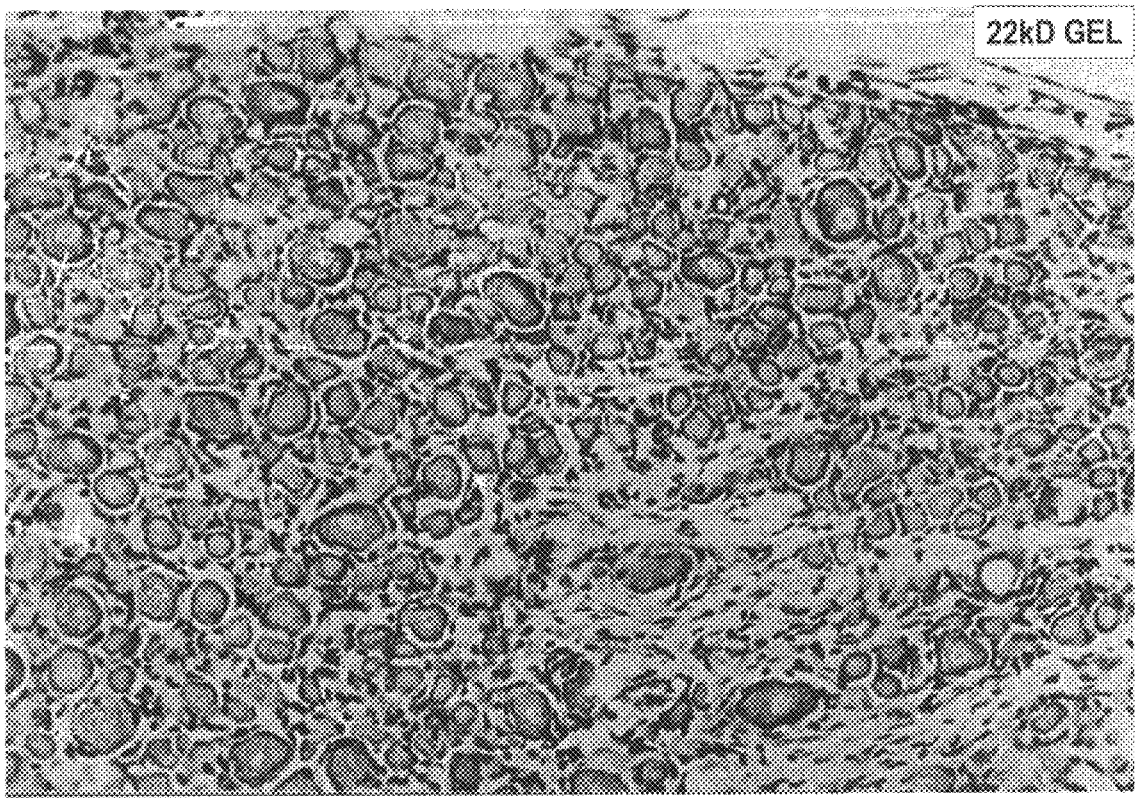
Figure 12D:
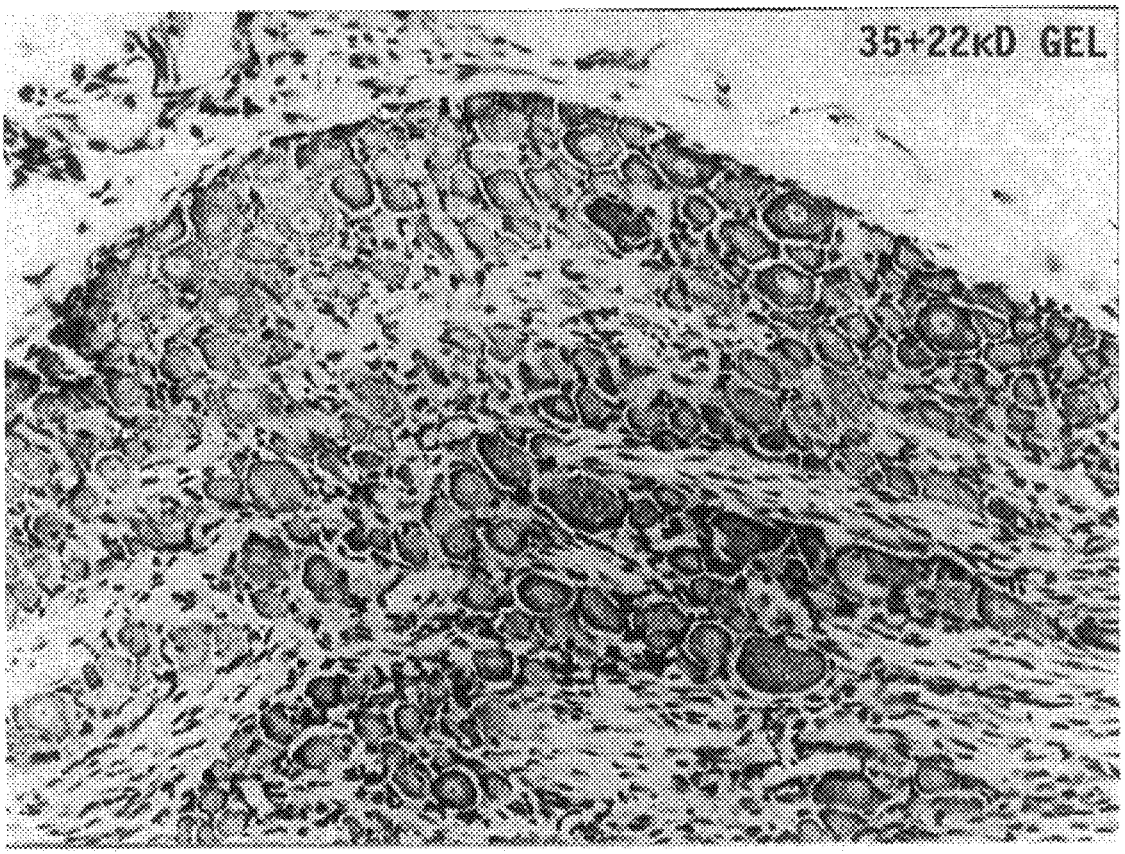

FIGS. 11A and 11B depict the results of the in vivo effect of muscle-derived motoneuronotrophic factors on neuronal survival and viability following the transection of the rat facial nerve in the presence of either goat anti-rabbit IgG or an anti-35 kD monoclonal antibody in tabular and histogram form, respectively. The development of the anti-35 kD MNTF1 monoclonal antibody will be discussed in a subsequent section herein. The goat anti-rabbit IgG was utilized as a control to ensure that there was no inhibition of the biological activity of the 35 kD MNTF1 protein due to non-specific interactions. Results indicated that ~80% of the motoneurons associated with the facial nerve were still viable after a 2 week period. In contrast, a marked reduction in motoneuron viability (50% viability after 2 weeks) was found when an anti-35 kD MNTF1 monoclonal antibody was utilized. Therefore, the diminution of neuronal viability appeared to be a function of the inhibition of the 35 kD MNTF1 protein by the anti-35 kD MNTF1 monoclonal antibody.

FIGS. 12A–D are a series of four photomicrographs depicting the in vivo effects of MNTFs on neuronal survival and viability following the transection of the dorsal root ganglion in Sprague Dawley rats. In this series of experiments, axotomized dorsal root ganglion were cut in the right side of 10 day-old Sprague Dawley rats. The left-side dorsal root ganglion were left intact to serve as an internal contralateral control. Sections of MNTF1-containing or MNTF2-containing PhastGel (~2×3 mm section containing 5–30 ng of MNTFs) were applied via implantation to the axotomized sites. As before, the MNTF1 and MNTF2 correspond to the 35 kD and 22 kD proteins, respectively. PhastGel sections without MNTFs were implanted in axotomized animals in an analogous manner, and served as controls. Results demonstrated that without the presence of either MNTF1 or MNTF2, only ~40% of the motoneurons remained viable (see FIG. 12A). In contrast, 60–70% remained viable in the presence of MNTF1 (see FIG. 12B), MNTF2 (see FIG. 12C) or both MNTF1 and MNTF2 (see FIG. 12D).

Figure 13:
FIG. 13 shows a hemisection of the spinal cord at the T1–T3 level in the adult Sprague Dawley rat depicting the surgical autographing of the ulnar nerve to the ventral spinal cord and the median nerve to the dorsal spinal cord.
Figure 13:
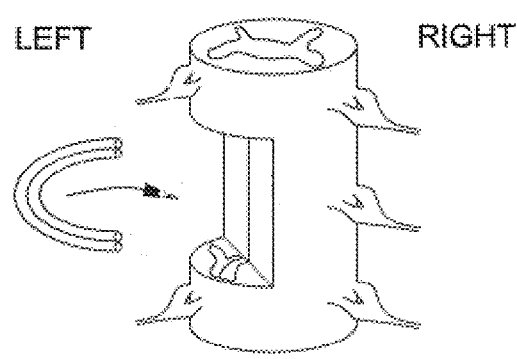
Figure 14:
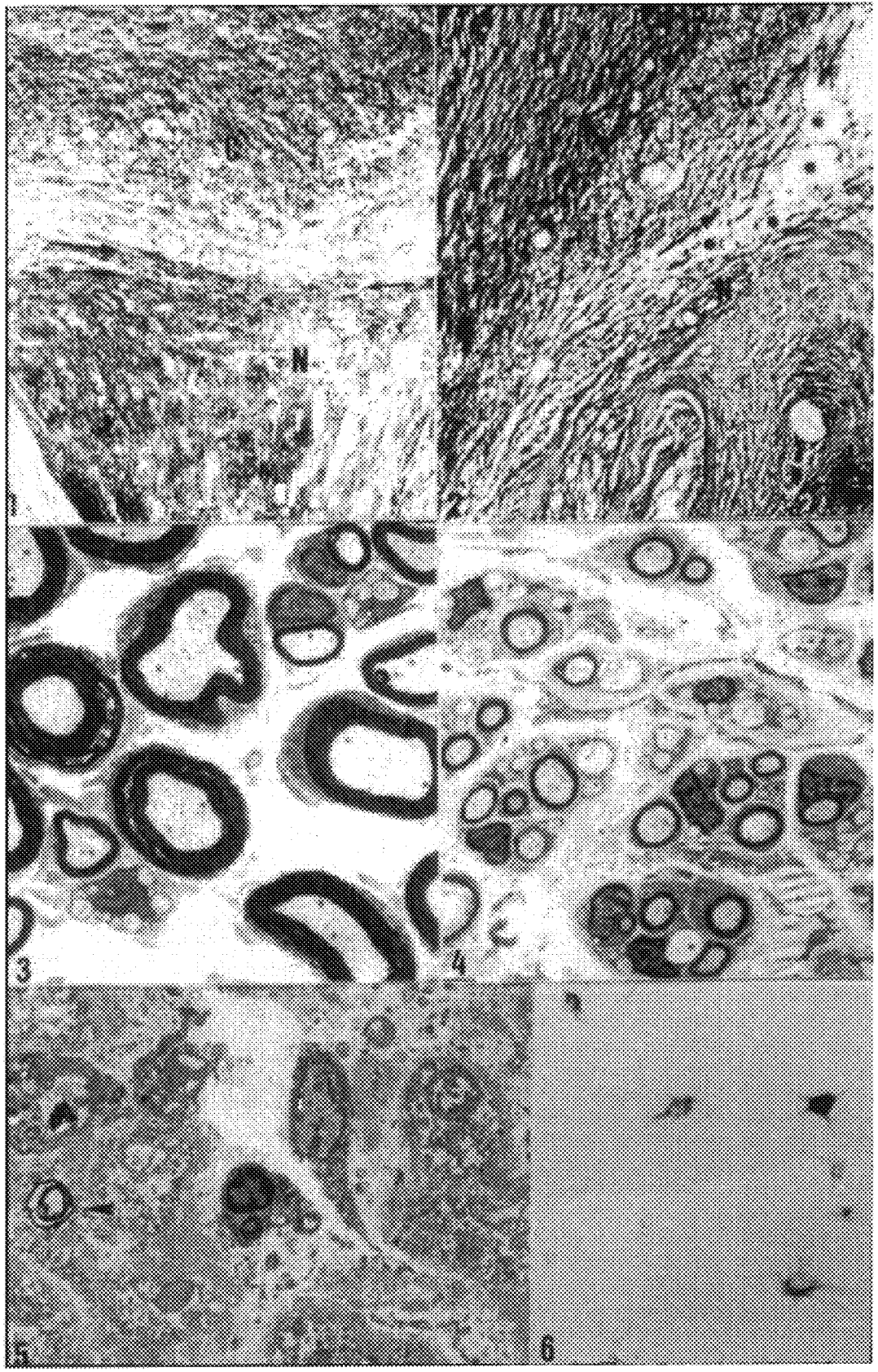
FIG. 14 (panels 1–6) depicts the trophic and rescuing effects of MNTFs on the survival of motoneurons following the hemisection of the spinal cord in Sprague Dawley rat with nerve autographs. Panels 1–4 demonstrate that: (1) with the presence of MNTF1 & MNTF2 there were reduced in inflammation, scar formation, and white blood cells infiltration at the junction of the autograph nerve (N) and the spinal cord (C); panel (2) with no MNTFs there were increased in scar formation, inflammation, and WBCs infiltration at the junction of the autograph nerve (N) and the spinal cord (C); panel (3) is an electron micrographs of the autograph nerve with MNTFs which reveals an increase in number and size of the regenerating nerve fibers with healthy myelination; panel (4) is an EM of the autograph nerve without MNTFs which reveals no healthy myelinated regenerating nerve fibers.

In Vivo Testing of MNTF1 and MNTF2 in Hemi-sectioned Spinal Cords with Nerve Autographs In the next series of experiments, depicted in FIG. 13 and FIG. 14 (panels 1–6), rat MNTF1 and MNTF2 were tested in vivo in hemi-sectioned spinal cord rats with peripheral nerve autographs. Following anesthesia with barbitol, the left side of the spinal cord of adult Sprague Dawley rats were hemi-sectioned at the T1–T3 (8 mm) level. Under a dissection microscope, 20 mm long ulnar and median nerve trunks from the left fore limb were dissected and grafted onto the T1–T3 region of the spinal cord at the lateral-ventral and lateral-dorsal portions, respectively [see FIG. 13]. The nerve grafts were anchored to the spinal cord by suturing their associated membranes together with 10-0 thread. In the experimental group, a total of 16 sections (~1×1 mm) of MNTF1-containing and MNTF2-containing PhastGel were placed in close proximity to the junctions of the nerve grafts and spinal cord. In a control group, PhastGel sections without MNTFs were implanted in an analogous manner.

Results revealed that, in the presence of the MNTF 1-containing and MNTF2-containing PhastGel sections [see FIG. 14, panels 1 and 3, respectively], the survival rate, the overall recovery rate, the numbers of both regenerated myelinated and unmyelinated nerve fibers, and the number of surviving motoneurons of the hemi-sectioned rats [see FIG. 14, panel 3] were far greater than those exhibited by the control group without the presence of MNTFs [see FIG. 14, panels 2 and 4]. The results were obtained by both general and histological observations which were recorded and compared. With respect to general observations, the rat's ambulatory ability (i.e., the ability to crawl or walk) and reaction to digit compression were recorded. Histological observations included determination of inflammatory response (presence of infiltrating macrophages, lymphocytes, and scar tissue), morphology and ultrastructure of neurons, the presence of myelinating Schwann cells, and the presence of myelinated nerves. The results demonstrated that the experimental animals treated with MNTFs recovered both motor and sensory neuronal function in a far more efficacious manner than the control animal group. The experimental animal group also exhibited minimal inflammatory response, little or no scar tissue formation, normal Schwann cell morphology, and normal myelinated and unmyelinated nerve morphology [see FIG. 14, panel 3]. In contrast, the control animal group exhibited an inflammatory response, indicated by large numbers of infiltrating macrophages/lymphocytes and collagen-containing scar tissue formation at the location of the neuronal graft [see FIG. 14, panel 5]. Furthermore, the Schwann cells of the control animal group were either non-viable or exhibited a swollen morphology with vacuolations [see FIG. 14, panel 2].

In addition, subsequent experimental results demonstrated that the application of MNTF1 and/or MNTF2 significantly increased the amount, size, and neuronal shape of the regenerated myelinated nerve fiber. From these results it may be postulated that MNTFs play a role in the biosynthesis of the various protein constituents of myelin (e.g., myelin basic proteins, Wolfgram proteins, etc.). Decreases in the concentrations of these proteins is implicated in several degenerative diseases of myelinated nerve fibers.

In Vivo Testing of Rat MNTF1 and MNTF2 in Hereditary Motoneuron Disease

The molecular mechanism for human motoneuron diseases, including Amotrophic Lateral Sclerosis (ALS) and Spinal Muscular Atrophies (SMA) have not yet been elucidated. However, the wobbler mouse (genotype wr/wr) has been developed and is widely used as an animal model for studies involving spinal and brainstem motoneuron diseases. See e.g., Duchen, L. W. and Strich, S. J., An Hereditary Motor Neuron Disease with Progressive Denervation of Muscle in the Mouse: The Mutant "Wobbler," 31 *J. Neurol. Neurosurg. Psychiatry*, 535 (1968); La Vail, J. H., et al., Motoneuron Loss in the Abducens Nucleus of Wobbler Mice, 404 *Brain Res.* 127 (1987), whose disclosures are incorporated herein by reference. The wobbler mouse carries an inherited autosomal double-recessive gene mutation in Chromosome 11 (specifically located between the egfr and rel genes), which leads to the progressive degeneration of spinal and brainstem motoneurons. See Kaupman, K., et al., 13 *Genomics* 35 (1992), whose disclosure is incorporated herein by reference.

Approximately 3 week post-partum, wobbler mice begin to develop the "wobbling" symptomology (stage 1) with concomitant degeneration of cervical motoneurons leading to both the wasting of the muscles of the forelimbs and an inability to extend the digits and claws. By 3 months of age, the pathologic symptomology will progress to stage 4, with a "clumping together" of all associated joints in the forelimbs (e.g., the wrist, elbow, and shoulder joints), as well as an extensive loss of body weight and chronic fatigue. Frequently, however, most wobbler mice die prior to reaching 3 months of age.

The wobbler mouse model has been utilized in demonstrating the limited protective effect of several trophic factors on the degeneration of motoneurons including: (i) the Ciliary Neurotrophic Factor (CNTF; see e.g., Sendner, M., et al., Ciliary Motoneurotrophic Factor Prevents the Degeneration of Motor Neurons After Axotomy, 345 *Nature* 440 (1990)), (ii) the Brain-Derived Neurotrophic Factor (BDNF; see e.g., Oppenheim, R. W., et al., Brain-Derived Motoneurotrophic Factor Rescues Developing Avian Motoneurons From Cell Death, 360 *Nature* 755 (1992)), (iii) the Ganglion-Derived Neurotrophic Factor (GDNF; see e.g., Henderson, C. E., et al., GDNF: A Potent Survival Factor for Motoneurons Present in Peripheral Nerve and Muscle, 266 *Science* 1062 (1994), and (iv) the combination of CNTF and BDNF (see e.g., Mitsumoto, I. L., et al., 265 *Science* 1107 (1994)). In these aforementioned studies, the treated wobbler mice were administered with milligram (mg) concentrations of the corresponding trophic factor at each dosing, with a treatment schedule consisting of several dosings per week for a period of a number of weeks. In most cases, response by the wobbler mice to treatment with the trophic factor (as measured by improvement of motor function) were scored during a one month time period. Interestingly, however, the trophic factor-treated mice frequently died sooner than the control wobbler mice which did not receive treatment. See e.g., Ikeda, S., et al., Histometic Effects of Cilliary Neurotrophic Factor in Wobbler Mouse Motor Neuron Disease, 37 *Ann. Neurol.* 47 (1995); Ikeda, S., et al., Effects of Brain-Derived Neurotrophic Factor on Motor Dysfunction in Wobbler Mouse Motor Neuron Disease, 37 *Ann. Neurol.* 505 (1995).

The "negative" results demonstrated by these aforementioned trophic factor studies raise the question of whether these investigators were working with the appropriate trophic factor(s) and/or the appropriate biological assays. Therefore, based upon the documented relationship between motoneurons and their associated target muscles, the inventor of the invention disclosed herein chose to isolate and purify the motoneuronotrophic factors (MNTF1 and MNTF2) identified by the motoneurons themselves from the target tissue of the respective motoneuron (i.e., the skeletal muscle); and to study the survival curve of the treated wobbler mice after only a single dose of MNTF1 administered at nanogram (ng) concentrations for a period of one year. It should be noted that the MNTF concentration utilized in this study was 1000-times less (i.e., ng versus mg concentrations) than that utilized in previous studies involving several other motoneuronotrophic factors (e.g., See e.g., Ikeda, S., et al., Histometic Effects of Cilliary Neurotrophic Factor in Wobbler Mouse Motor Neuron Disease, 37 *Ann. Neurol.* 47 (1995); Ikeda, S., et al., Effects of Brain-Derived Neurotrophic Factor on Motor Dysfunction in Wobbler Mouse Motor Neuron Disease, 37 *Ann. Neurol.* 505 (1995)).

Figure 15A:
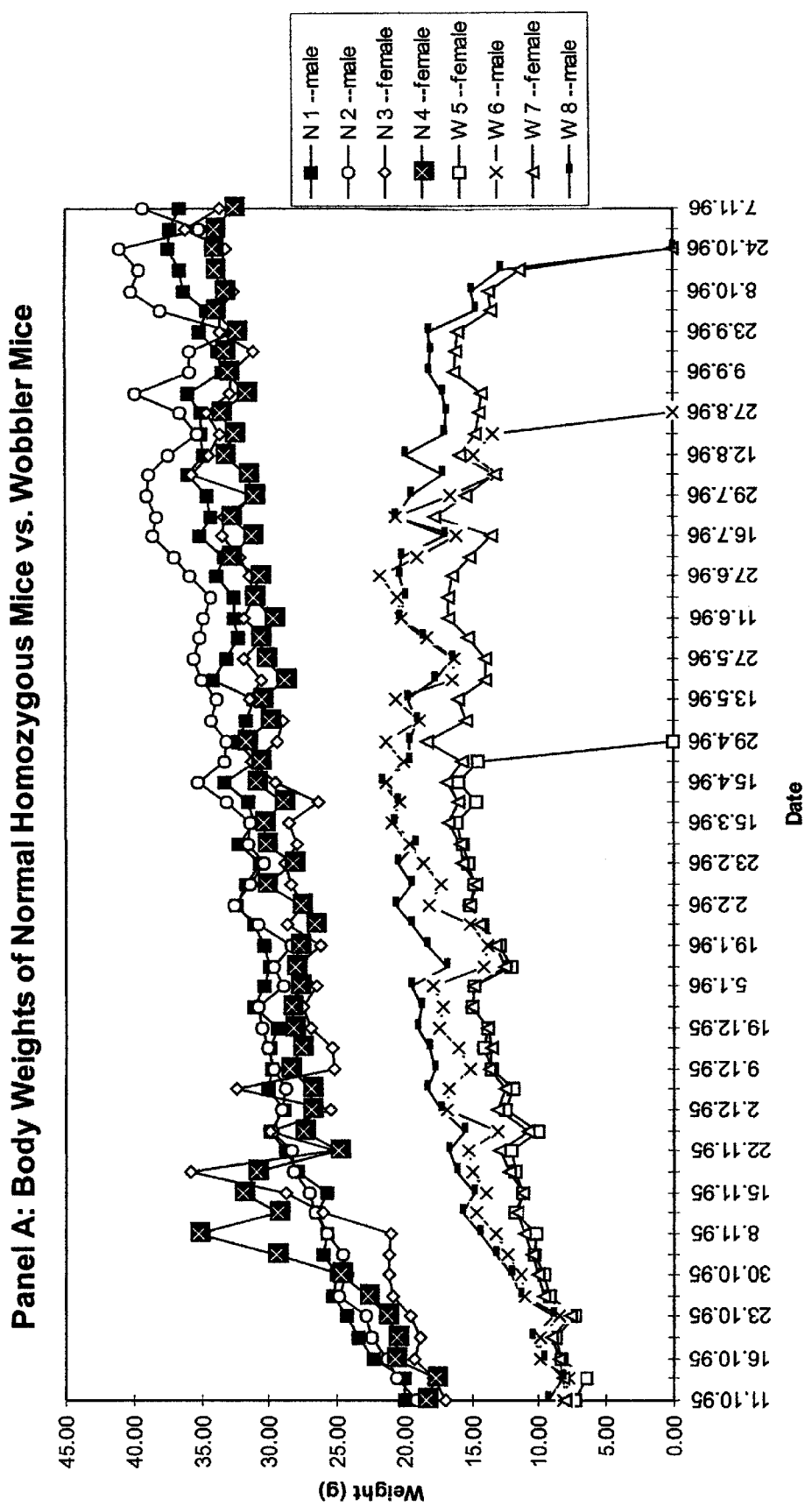
FIGS. 15A and 15B depict the body weights of homozygous (N1–N4) in panel A and heterozygous (N1–N4) in Panel B wild type mice verses the body weights of their litter-mates wobbler mice which were treated with rat MNTFs (W5–W8) and (W1–W4), respectively.
Figure 15B:
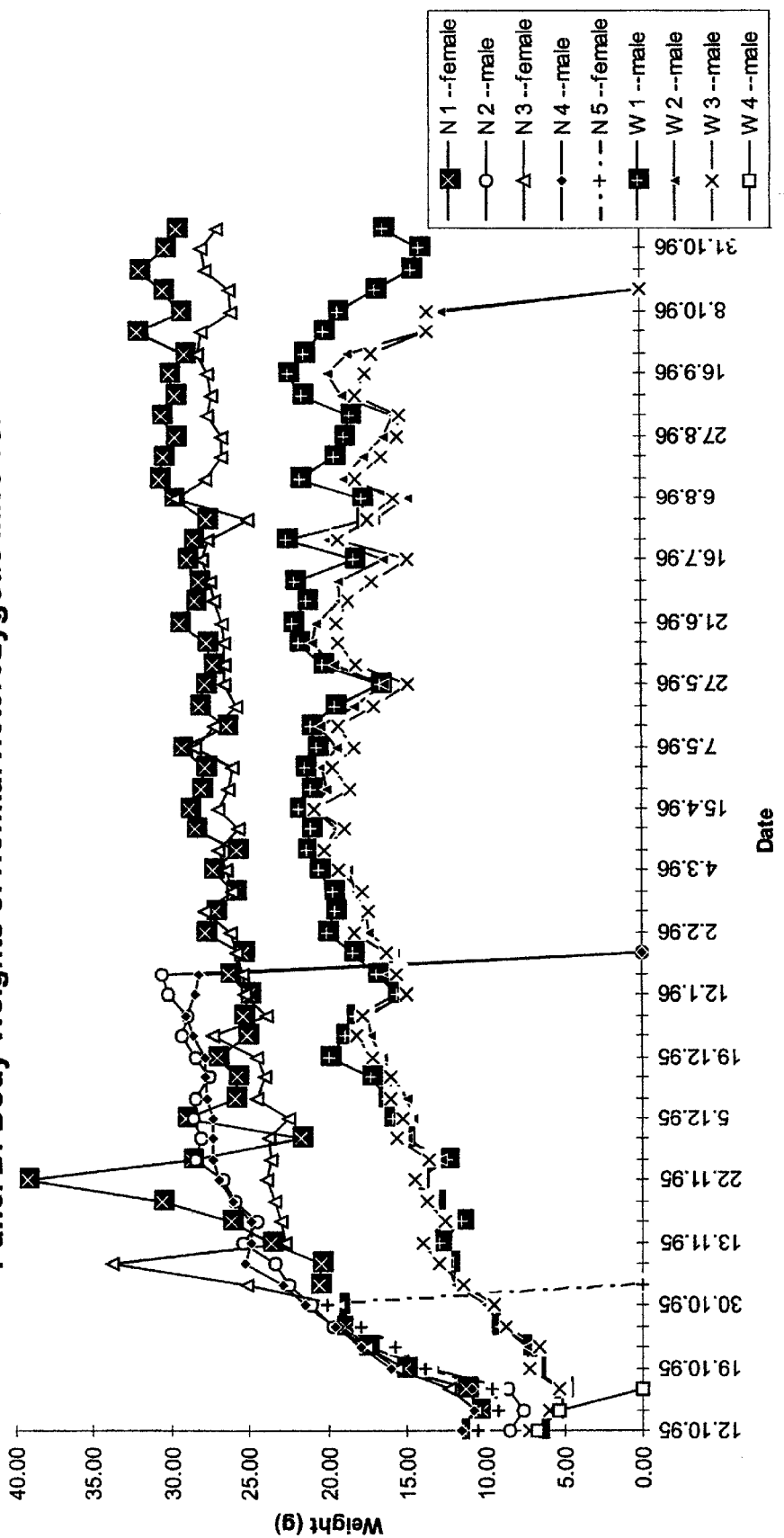

In a series of experiments, depicted in FIGS. 15A and 15B, in vivo testing of rat MNTF1 and MNTF2 in hereditary motoneuron disease was performed in wobbler mice. Wobbler mice are animals (developed at and kindly provided by the National Institutes of Health (NIH) in Bethesda, Md.) which possess double recessive genes (wr/wr) for a hereditary motoneuron disease. The motoneuron disease manifests itself with symptoms of upper limb neuromuscular failure which initially appears approximately 3 weeks after birth. The condition also affects the animals body weight, general health conditions, respiration, and life span in a deleterious manner. The disease gradually progresses to the final stage (stage 4) by 3 months of age, with an associated dramatic increase in animal mortality.

Sections (~2×6 mm) of MNTF1-containing and MNTF2-containing PhastGel were finely minced and applied to the wobbler mice via implantation of the aforementioned MNTF-containing PhastGel sections between the trapezius and rhomboid muscles at the C7-T3 region of the spinal cord. A control group of wobbler mice received PhastGel sections without MNTFs. Results indicated that the application of a single "dose" (35 μg/kg body weight) of MNTF-containing PhastGel to 6 week old wobbler mice arrested the progression of the symptomology of the motoneuron disease to that associated with the initial stage (stage 1) for a period of observation up to 10 months. Additionally, in comparison to the control animal group, the experimental animals demonstrated a general improvement in health, respiration, body weight, strength of fore limbs, as well as the general prevention of deterioration of health, respiration, neuromuscular activities of the fore limbs, and the vacuolation and chromatolysis of their cervical motoneurons. In conclusion, these results are illustrative of rat MNTFs arresting the further symptomatic development of hereditary motoneuron disease in wobbler mice.

FIGS. 15A and 15B graphically depicts the weights of homozygous and heterozygous wild type mice verses wobbler mice. In this series of experiments, the body weights of four "normal" homozygous mice (A) and four heterozygous mice (B) were compared with the body weights of four each homozygous wobbler mice (W1–W4) and (W5–W8). Each of the wobbler mice were treated with rat MNTF1 and MNTF2, whereas the "normal" mice were left untreated. While, the overall body weights of the wobbler mice were generally less than that of "normal" animals, the wobbler mice nonetheless exhibited consistent weight gain and increased longevity. In contrast, untreated wobbler mice did not demonstrate this type of consistent weight gain and usually die at approximately 3 months of age. It should be noted that the abrupt "drop-points" in both FIGS. 15A and 15B represent the date on which that particular animal expired. Therefore, in conclusion, these results indicate that treatment with the MNTFs had a dramatic impact on the hereditary motoneuron disease in wobbler mice.

The elucidation of the relationship between the individual muscle fibers and their associated motorneurons is of paramount importance in understanding such diseases as multiple sclerosis (MS), muscular dystrophy (MD), and myasthenia gravis (MG). In a related series of experiments, it was demonstrated that the application of MNTF1 and/or MNTF2 which resulted in a marked regeneration of the motorneurons concomitantly led to the recovery associated muscle fibers formation. Moreover, neuro-stimulation of the muscle fiber to promote the growth, survival, and regeneration of the muscle fiber, as well as for the putative production of muscle-derived MNTFs, plays an extremely important role in the cyclic relationship between motorneurons and the muscle fibers.

Development of Monoclonal Antibodies for MNTF1 and MNTF2

Monoclonal antibodies specific for rat MNTF1 and MNTF2 were prepared. The 35 kD (MNTF1) and 22 kD (MNTF2) protein-containing bands were excised from a Phast System gel (1×30 mm gel sections containing 100 ng motoneuronotrophic factor) and utilized as antigens in the immunization of separate groups of Balb/c mice. Specifically, the MNTF-containing PhastGel sections were excised and finely minced. The PhastGel pieces were then mixed with an equal volume of complete Freund's adjuvant and directly injected intraperitoneally into the Balb/c mice. A total of three antigen immunizations were performed, with intraperitoneal injections of MNTF1-containing and MNTF2-containing PhastGel in physiological saline on the 7th and 21st day following the initial immunization. The spleens of the Balb/c mice were harvested and allowed to fuse with either NS-1 or SP2/0 myeloma cells. The resultant hybridomas were then screened utilizing MTT microassays and microscopic examination to select the most efficacious monoclonal antibodies capable of blocking the function of the MNTF1 and MNTF2 neuronotrophic factors. For example, from the 35 kD (MNTF1) fusions, a total of 8 hybridomas were selected and subsequently developed out of a total of 480 wells producing monoclonal antibodies specific for this aforementioned MNTF1 protein.

Immunoselection of Recombinant Human MNTF1

The selected MNTF-blocking monoclonal antibodies were next utilized to immunoselect clones of human motoneuronotrophic factor. The blocking monoclonal antibody for the human motoneuronotrophic factor (MAb-MNTF)

was used as an immunoprobe in the screening of positive expression clones from a selected human retinoblastoma cDNA library (produced by Clontech Co., Palo Alto, Calif.). In brief, the immunoselection/immunoprecipitation procedure for the cDNA library involved the isolation of mRNAs from cells of the Rb Y-79 retinoblastoma cell line. Reverse transcription reaction were performed to synthesize cDNAs utilizing the isolated retinoblastoma mRNAs as templates. The cDNAs were ligated into a Lambda phage vector (gt-11) and subsequently transformed in an E. coli strain Y1090 host bacteria.

The immunoscreening procedure utilized was a modification of that described in Young, R. A., and Davis, R. W., Efficient Isolation of Genes Using Antibody Probes, 80 Proc. Nat'l Acad. Sci. USA 1194 (1983), whose disclosure is incorporated herein by reference. The modification consisted of using ammonium nickel sulfate as an enhancing agent to increase 100-fold the sensitivity of the peroxidase-avidin-biotin complex reaction utilizing diamino-benzidine as the substrate. A maximum of 4 nitrocellulose membrane "replicas" were made from each colony plate for immunoscreening and only the most intensely-stained clones were selected in the immunoscreening procedure. The selected clones were then allowed to express their recombinant human proteins which were subsequently assayed to determine their potential MNTF biological activity in culture. The clone which displayed the highest MNTF-specific biological activity in motoneuron cultures was then selected for further analysis.

Immunohistochemical Localization of MNTF1 and the MNTF1 Receptor

Figure 5:
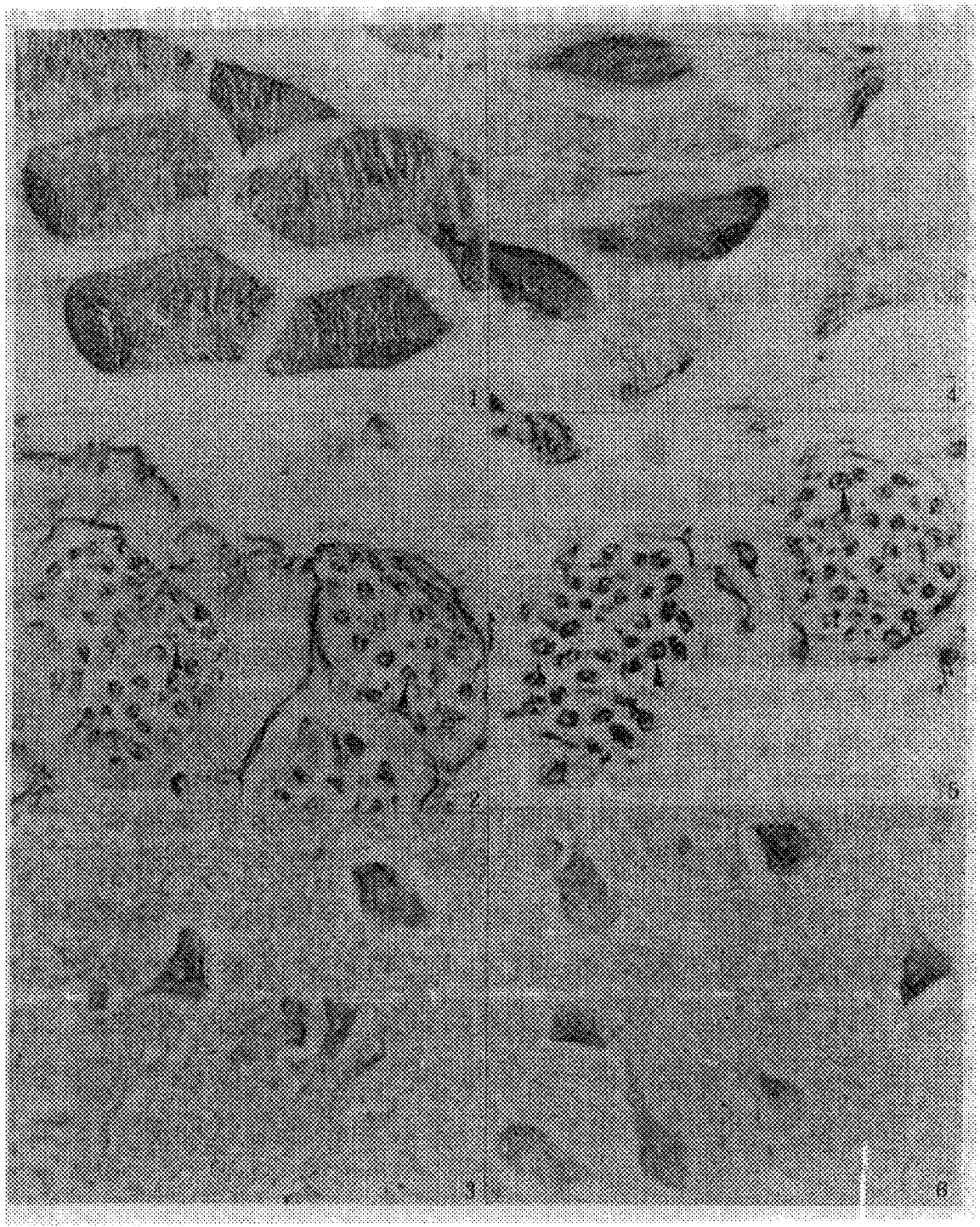
FIG. 5 (panels 1–6) reveals the immunohistochemical distribution of MNTF1 (panels 1, 3 & 5) and its putative MNTF1 receptor (panels 2, 4 & 6) in muscle (panels 1 & 2); Schwann cells (panels 3 & 4); and motoneurons (panels 5 & 6).

The MNTF1 monoclonal antibody was utilized to elucidate the immunohistochemical distribution of MNTF1 and the putative MNTF1 receptor in the peroneal muscle, Schwann cells, and motoneurons of 10 day-old Sprague Dawley rats. The procedure utilized was previously described in Ren, F. & Chau, R. M. W., Production and Assessment of Monoclonal Antibodies Specific for Rat Retinal Ganglion Neuronotrophic Factor, 7 J. Monoclonal Antibody 13 (1991). FIG. 5 demonstrates the results of this immunohistochemical localization of the MNTF1 protein (plates 1, 3 and 5) in peroneal muscle (plates 1 and 2), Schwann cells (plates 3 and 4) and motoneurons (plates 5 and 6). The results show an uneven distribution of fine, immunoreactive-positive "staining" among the muscle fibers with the more dense staining localized at the T-tubules, the motor end-plates, and the intervening nerve fibers. The striations of the individual muscle fibers were clearly visible without the utilization of a counter-stain. In addition FIG. 5 illustrates the immunohistochemical localization of the putative MNTF1 receptor (plates 2, 4, and 6).

Cloning and Sequence Analysis of Human Recombinant MNTF1

Figure 16:
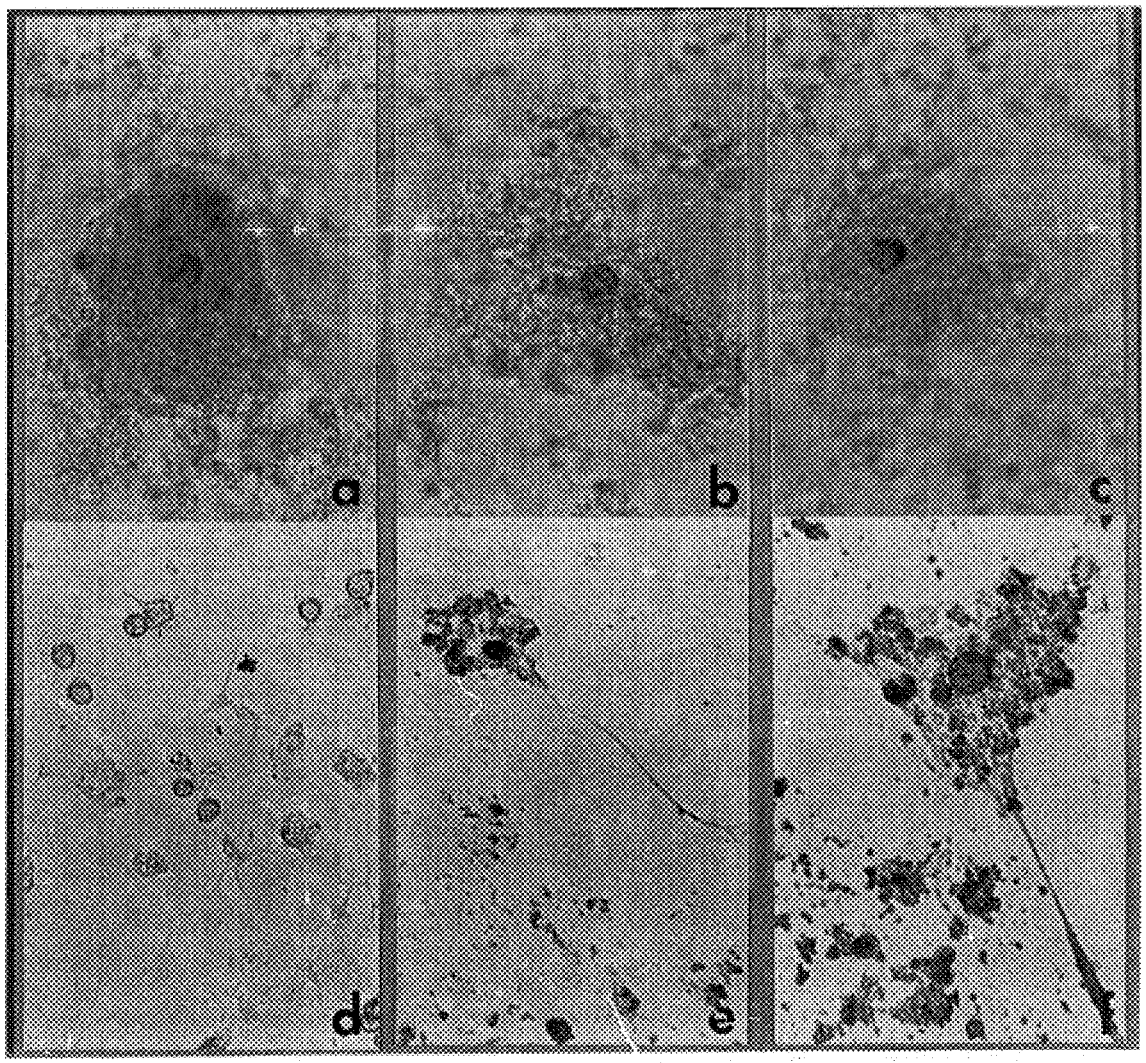
FIG. 16 (panels A–F) depicts the survival (with neurite outgrowth) of in vitro isolated anterior motoneuron cultures derived from the lumbar spinal cord following 14 days of co-culture with human recombinant MNTF1 (hrMNTF1). Panels a–c isolated motoneuron cultures were photographed at day 2 and panels d–e photographed at day 14; panels a and d represent control cultures with no hrMNTF1; and panels b, c, e, and f depict experimental cultures with hrMNTF1.

Human recombinant MNTF1 (hrMNTF1) was tested in vitro for potential biological activity with isolated anterior horn motoneurons in the following manner [see FIG. 16, panels A–F]. Anterior horn motoneurons were isolated from the lumbar spinal cord gray matter of 10 day-old Sprague Dawley rats following digestion in a 0.08% collagenase solution in DMEM medium containing 15% fetal calf serum. Following collagenase digestion, the anterior horn motoneurons were cultured in DMEM medium supplemented with 15% fetal calf serum. Results indicated that the anterior horn motoneurons co-cultured with hrMNTF1 remained viable and exhibited higher levels of neurite outgrowth [see FIG. 16, panel E and panel F] than that of the control cultures without hrMNTF1 [see FIG. 16, panel D]. Viability and neurite outgrowth were determined utilizing both MTT microassay and microscopic examination as previously described.

The cloned, recombinant human MNTF1 in gt-11 phage vector (designated as Lambda.35KD.MNTF1) was expressed in E. coli strain Y1090. It was found, in vitro, to be capable of reducing, by a factor of 3-fold, the overall numbers of isolated anterior horn motor neurons which entered into apoptosis (the process of cellular "dying") as evidenced by a lack of cellular fragmentation into apoptotic bodies and the condensation of chromatin in the pyknotic nucleus. In addition, hrMNTF1 supported the growth and "spreading" of the motoneurons into giant, active neurons with extended growth cone-containing axons [see FIG. 16, panels E and panel F]. In contrast, the control motoneuron cultures, lacking expressed hrMNTF1, many non-neuronal cells (e.g., glial cells and fibroblasts) were actively growing after 10 days of culture in DMEM medium supplemented with 15% fetal calf serum [see FIG. 16, panel D], yet there was a complete lack of viable, growing motoneurons in these control cultures.

The cDNA insert of the Lambda.35KD.MNTF1 clone was then sub-cloned into an in vitro expression vector system and its DNA sequence was elucidated by the following a methodologies:

1. Preparation and Purification of Lambda.35KD.MNTF1

10 plaque-forming units (pfu) of Lambda.35KD.MNTF1/gt 11 phage was inoculated into a 500 ml overnight culture of E. coli stain Y1090 until complete lysis of the bacteria was observed. The Lambda phage were recovered and purified by centrifugation and enzymatic treatment with RNase and DNase in an NaCl/PEG 8000 solution, followed by high speed CsCl density gradient centrifugation to collect the purified phage at a final gradient density of approximately 1.5 gm CsCl/ml.

Isolation and purification of the Lambda.35KD.MNTF1 DNA was facilitated by initial digestion of the Lambda phage (1 ml) in EDTA, SDS, and proteinase K, followed by repeated extractions with phenol, phenol/chloroform, and chloroform. The DNA was then ethanol precipitated with 95% ethanol and collected by centrifugation. Following repeated washes in 70% ethanol, the Lambda.35KD.MNTF1 DNA pellet was redissolved in Tris-EDTA buffer.

2. Recovery of 35KD.MNTF1 cDNA from Lambda.35KD.MNTF1 DNA 10 g of Lambda.35KD.MNTF1 DNA was digested overnight with EcoR1 and the cleaved 35KD.MNTF1 cDNA was recovered via agarose gel electrophoresis. Following electrophoresis, the DNA bands were visualized utilizing U.V. light. Results of the EcoR1 digestion demonstrated the presence of two discreet DNA fragments—a 1.44 Kbp fragment designated 35F3 and a 0.93 Kbp fragment designated 35F6. The two DNA bands were individually excised from the agarose gel and the DNA was recovered via standard techniques. The recovered DNA was then prepared for subsequent DNA sequencing by recombination with M13 phage and for High Protein Expression by recombination with the pGEX-1 Lambda T EcoR1/BAP vector.

3. DNA Sequencing of the 35F3 and 35F6 DNA fragments of 35KD.MNTF1 cDNA

Following recombination of the 35F3 and 35F6 fragments with M13, the Dideoxy Nucleotide Chain Termination DNA Sequencing Methodology of Sanger (utilizing Bst DNA polymerase) was employed to elucidate the DNA sequence of the two MNTF1 DNA fragments. See Sanger, F., et al., Nucleotide Sequence of Bacteriophage DNA, 162 *J. Mol. Biol.* 729 (1982), whose disclosure is incorporated herein by reference. This sequencing methodology provided extremely accurate and reproducible results with respect to the DNA sequencing of the two EcoR1-generated fragments of the 35KD.MNTF1 cDNA fragments and indicated that the 35F3 fragment consisted of 1443 base pairs; whereas the 35F6 fragment was found to consist of 927 base pairs.

FIG. 1A depicts the DNA sequence (SEQ ID NO:1) of the 35F3 DNA fragment (1443 bp). By standard convention the DNA sequence is shown in the 5' to 3' orientation. The 35F3 clone was constructed by EcoR1 digestion of the Lambda 35KD.MNTF1 clone. The resulting 35F3 EcoR1-generated fragment was then recombined with M13 for subsequent DNA sequencing utilizing the aforementioned Sanger methodology.

FIG. 1B depicts the DNA sequence (SEQ ID NO:2) of the 35F6 DNA fragment (927 bp). By standard convention the DNA sequence is shown in the 5' to 3' orientation. The 35F6 clone was constructed by EcoR1 digestion of the Lambda 35KD.MNTF1 clone. The resulting 35F6 EcoR1-generated fragment was then recombined with M13 for subsequent DNA sequencing utilizing the aforementioned Sanger methodology.

4. Sub-cloning of the 35F3 and 35F6 EcoR1-generated MNTF1 DNA Fragments

The 35F3 (1443 base pairs) and 35F6 (927 base pairs) EcoR1-generated MNTF1 DNA fragments were sub-cloned into the pGEX-1 Lambda T EcoR1/BAP High Protein Expression vector [hereinafter pGEX]. The resultant subclones were designated MNTF1-1443 (35F3) and MNTF1-927 (35F6). The pGEX vector was selected due to the following factors: (i) it possessed a high efficiency transcriptional promotor at its 5'-terminus and a 3'-terminus poly(A) tail; and (ii) it provided an easy methodology for the purification of the MNTF1-1443 and MNTF1-927 recombinant proteins via affinity column chromatography-based purification of the glutathione-S-transferase (GST)-containing MNTF1 fusion proteins.

A. Transformation of Recombinant Plasmid

The pGEX vector was digested with EcoR1. The digested pGEX vector was then incubated overnight with the EcoR1-generated MNTF1-1443 and MNTF1-927 DNA fragments in the presence of T4 DNA ligase. Following ligation, competent *E. coli* strain DH5 were transformed with the recombinant vector and transferred onto Luria broth (LB) agar plates containing 100 g/ml ampicillin. Due to the fact that the pGEX vector contained a gene which conferred ampicillin resistance to the transformed bacteria, the use of ampicillin screening allowed the exclusive selection of transformed bacterial colonies, as only those bacteria containing the recombinant vector would be viable in its presence.

B. Identification and Isolation of MNTF1-1443 and MNTF1-927 Transformants

The transformed bacterial colonies were individually selected, inoculated into a small volume of LB medium containing 100 g/ml ampicillin, and incubated for approximately 3 hours. Following incubation, the transformed bacteria were collected via centrifugation for subsequent isolation of the recombinant vector DNA by the alkaline lysis "mini prep" technique as described in Maniatis, T., Fritsch, E. F., and Sambrook, J., *Molecular Cloning,* 2nd ed., Cold Spring Harbor Laboratory, Cold Spring Harbor, N.Y. pp. 134–136 (1986). With this technique, the collected bacteria were lysed by the addition of a Tris-EDTA/NaOH/SDS solution with vigorous vortexing. After centrifugation to collect contaminating cellular debris, the recombinant vector DNA-containing supernatant was aspirated, extracted with phenol and chloroform, and precipitated with 95% ethanol. The mixture was centrifuged to collect the precipitated DNA and the nucleic acid pellet was dissolved in Tris-EDTA buffer. Two recombinant species were identified: pGEX-MNTF1-1443 and pGEX-MNTF1-927.

The collected recombinant vector DNA was then digested with EcoR1 to release the 1443 bp MNTF1-1443 and 927 bp MNTF1-927 DNA inserts from the 4.9 Kbp pGEX vector. The digested DNA was subjected to agarose gel electrophoresis and the individual DNA bands were identified via U.V. light visualization.

"Positive" bacterial colonies (i.e., those which contained either the MNTF1-1443 or MNTF1-927 DNA insert) were selected and inoculated into LB medium for large scale plasmid purification via alkaline lysis and PEG precipitation. The purified recombinant vector DNA was then transfected into an *E. coli* strain BL-21 host bacterium to facilitate high levels of expression of human recombinant MNTF1-F3 (hrMNTF1-F3) and MNTF1-F6 (hrMNTF1-F6) proteins.

C. Expression and Amplification of hrMNTF1-F3 and hrMNTF1-F6 Fusion Proteins pGEX-MNTF1-1443 or pGEX-MNTF1-927 DNA were transfected into *E. coli* stain BL-21 competent bacteria in 50 ml of LB medium. IPTG was utilized to induce high levels of expression of the hrMNTF1-F3 or hrMNTF1-F6 proteins. Collected bacteria were lysed, frozen, and thawed a total of 4-times using liquid nitrogen, sonicated, and centrifuged. The supernatant, containing the hrMNTF1-F3 or hrMNTF1-F6 fusion proteins, was then passed through an anti-GST affinity chromatography column containing anti-GST monoclonal antibodies (Pharmacia). The use of this type of affinity chromatography allowed purification of the GST-hrMNTF1-F3 and GST-hrMNTF1-F6 fusion proteins which were bound to the matrix through the GST moiety. Following a high salt wash, the GST-hrMNTF1-F3 and GST-hrMNTF1-F6 fusion proteins were eluted. The proteolytic enzyme thrombin was utilized to cleave the linkage between the MNTFs and the GST moiety and the purified hrMNTF1-F3 and hrMNTF1-F6 proteins were collected for subsequent in vivo and in vitro assays and for amino acid sequencing.

In Vitro and In Vivo Testing of the Trophic Activity of hrMNTF1-F3 and hrMNTF1-F6

The human recombinant motoneuronotrophic factors (hrMNTFs) may be utilized either as fusion proteins or as purified proteins. To obtain the purified protein form of hrMNTF1-F3 and MNTF1-F6, the expression products of the pGEX-MNTF1-1443 or pGEX-MNTF1-927 plasmids are isolated as previously described. The expression products consist of fusion proteins which contain MNTF fused with glutathione-S-transferase (GST). The fusion protein is then purified on a GST-monoclonal antibody affinity chromatography column (Pharmacia) which specifically cleave the bond between the expressed trophic factor (MNTFs) and the GST moiety. The trophic factor is subsequently eluted from the column and may be utilized in the same manner as the purified "native" proteins, as described above.

Figure 17:
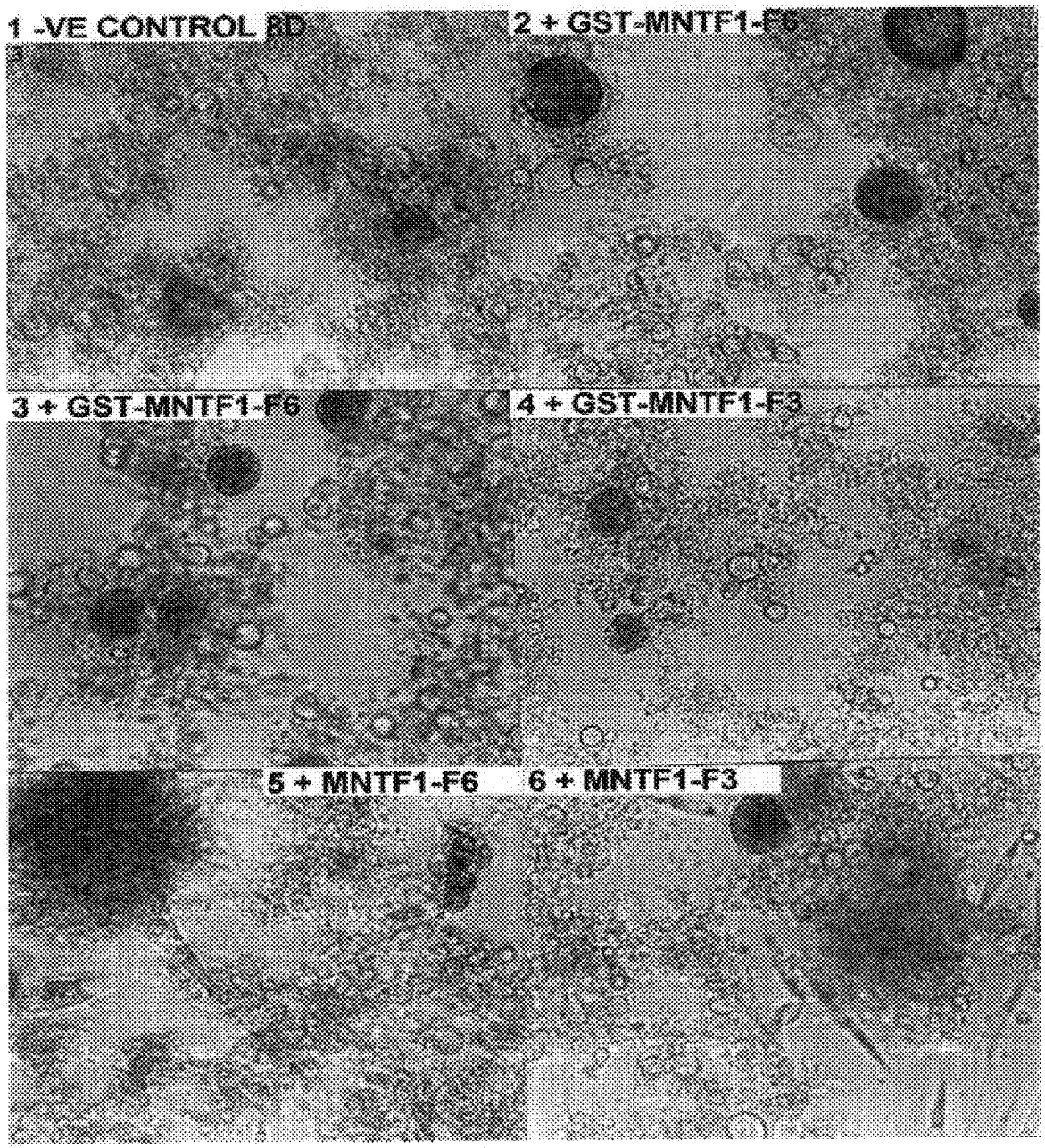
FIG. 17 (panels 1–6) depicts the survival of in vitro-isolated anterior motoneuron cultures derived from the lumbar spinal cord following 8 days of co-culturing without MNTF1-F6 (panel 1) and MNTF1-F3 (panel 2); with GST-fusion protein of MNTF1-F6 (panel 3) and MNTF1-F3 (panel 4); and with cleaved protein of MNTF1-F6 (panel 5) and MNTF1-F3 (panel 6). High magnification (×320).

Anterior horn motoneurons were isolated from the 10 day-old (postnatal) Sprague Dawley rat lumbar spinal cord via collagenase digestion in DMEM medium supplement with 15% fetal calf serum. FIG. 17 represents low magnification (100×) photomicrographs of the aforementioned anterior horn motoneurons cultured with varying concentrations of the GST-hrMNTF1-F3 (panel 4), GST-hrMNTF1-F6 (panel 3), and hrMNTF1-F3 (panel 6) and hrMNTF-F6 (panel 5) proteins with the GST moiety removed by thrombin proteolysis were added to the motoneuron cultures. Following 8 days of culture, it was observed that the motoneurons cultured in the presence of GST-conjugated or non-GST-conjugated hrMNTF1-F3 or hrMNTF1-F6 exhibited far greater growth patterns, as well as a marked decrease in the growth of associated non-neuronal cells, than those motoneurons cultured without either of these aforementioned proteins [see FIG. 17, panel 1 and 2]. The similarity of the results obtained between motoneuron cultures with hrMNTF1-F3 and hrMNTF1-F6 suggested that both pGEX-MNTF1-1443 and pGEX-MNTF1-927 may potentially possess the gene, or part of the gene which encodes the active site of a biologically active neurotropic factor.

Figure 18:
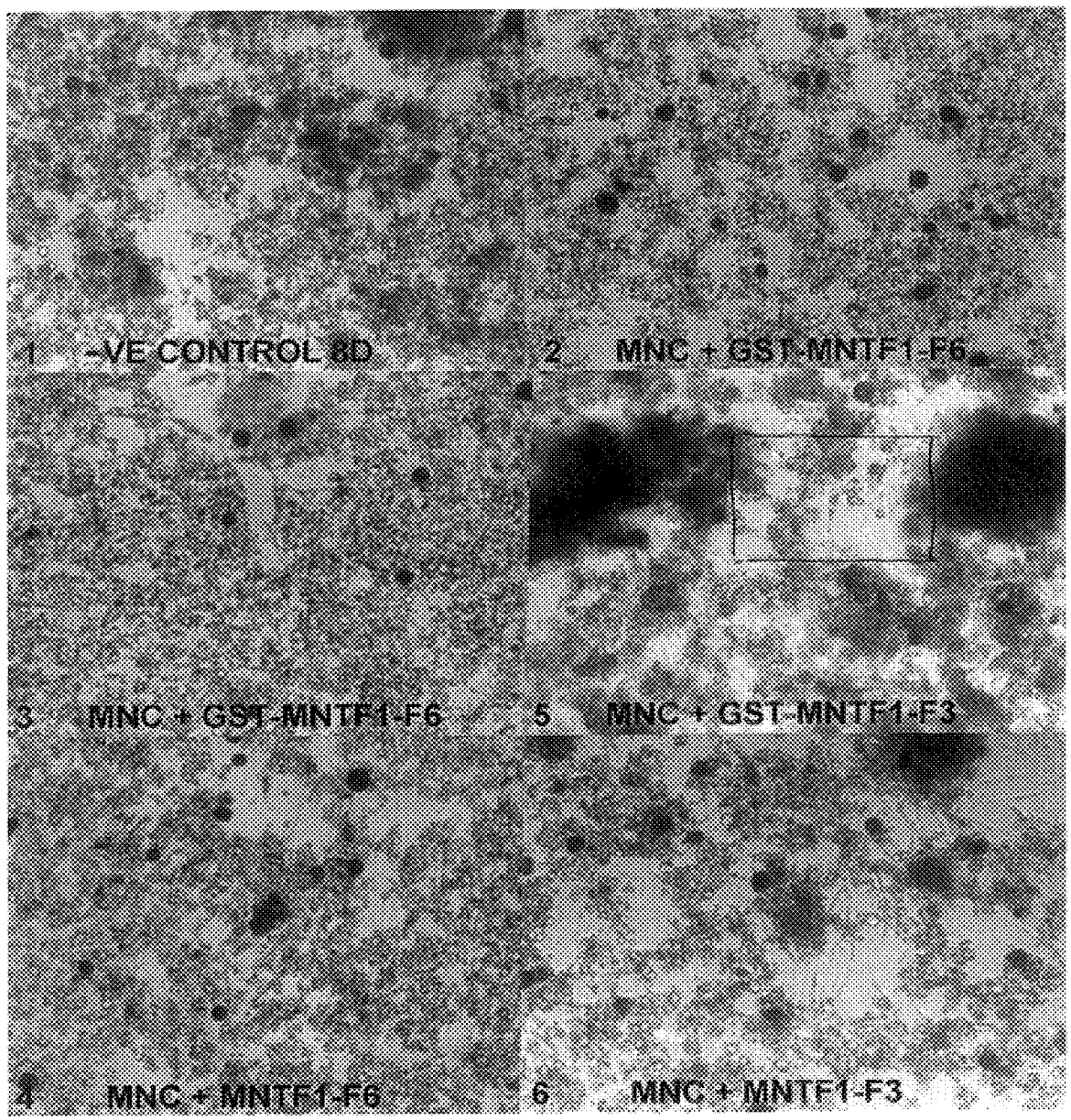
FIG. 18 (panels 1–6) depicts the survival (with neurite outgrowth) of in vitro-isolated anterior motoneuron cultures as in FIG. 17 (1–6) above. Low magnification (×100).

FIG. 18 depicts high magnification (320×) photomicrographs of the results initially illustrated in FIG. 17. It should be noted that panels 1–6 in FIG. 18 are identical to those panels shown in FIG. 17 with respect to the type of MNTF protein which was utilized in the co-culture with the isolated anterior horn motoneurons.

Figure 19:
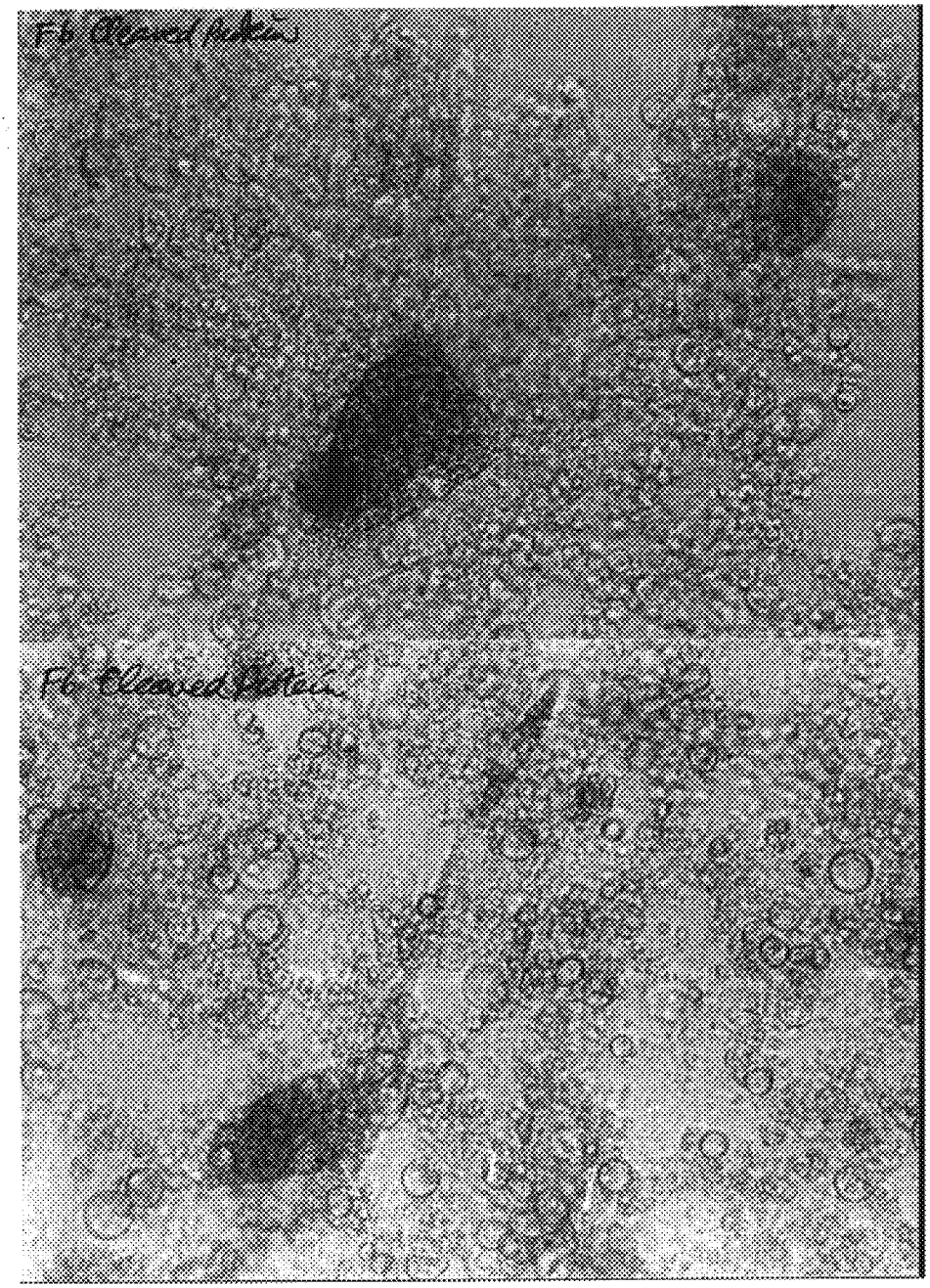
FIG. 19 (panels 1–2) depicts the survival with neurite outgrowth of in vitro-isolated anterior motoneuron cultures following 8 days of co-culturing with the cleaved protein of MNTF1-F6. High Magnification (×400).

FIG. 19 represents a high magnification (400×) photomicrograph of motoneuron viability and neurite outgrowth of in vitro-isolated anterior horn motoneurons cultured with hrMNTF1-F6 which has had the GST moiety removed by thrombin proteolysis.

Figure 20A:
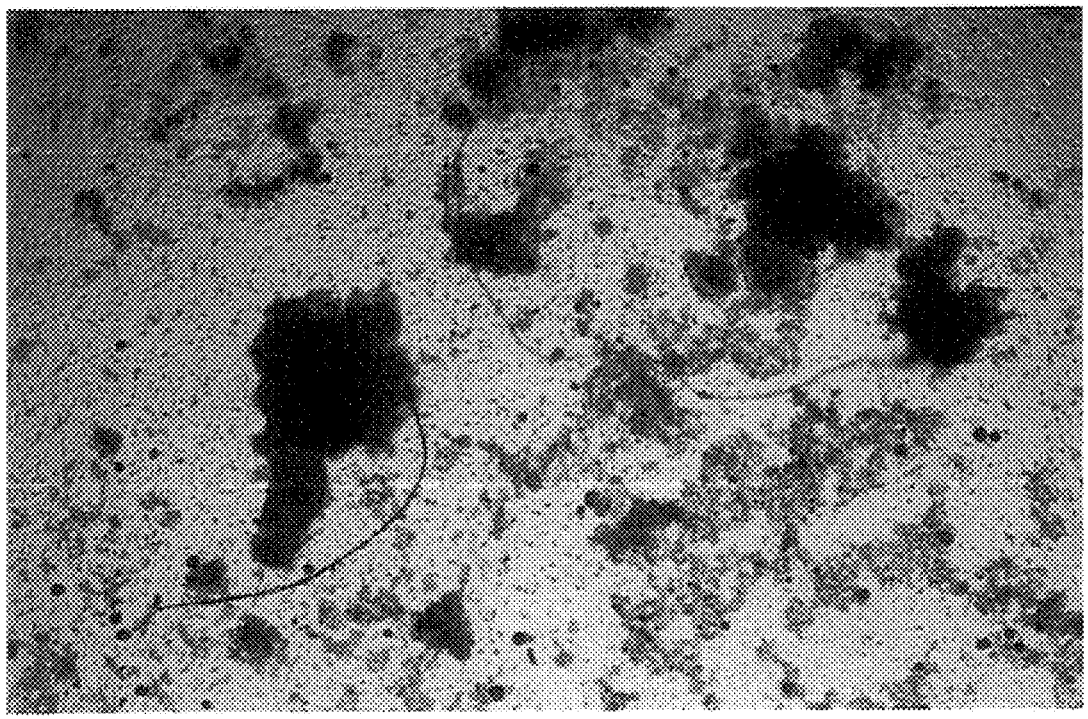
FIGS. 20A–D depicts the survival, growth and regeneration of myelinated nerve fiber from the in vitro-isolated anterior motoneurons from the culture as originally demonstrated in FIGS. 17 (panel 5), 18 (panel 5), and 19 (panels 1–2) after 21 days of co-culturing with the cleaved protein of MNTF1-F6.
Figure 20B:
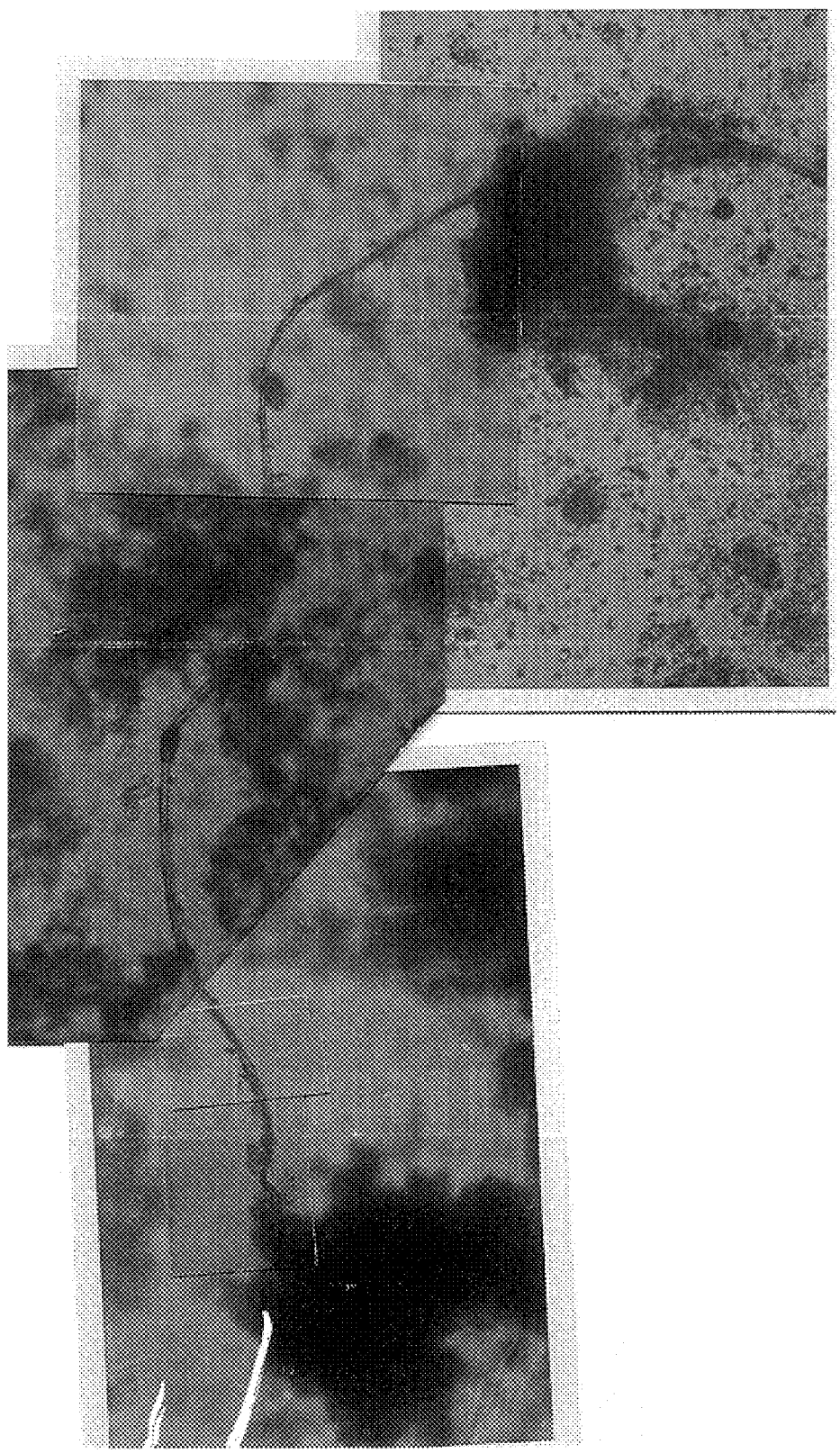
Figure 20C:
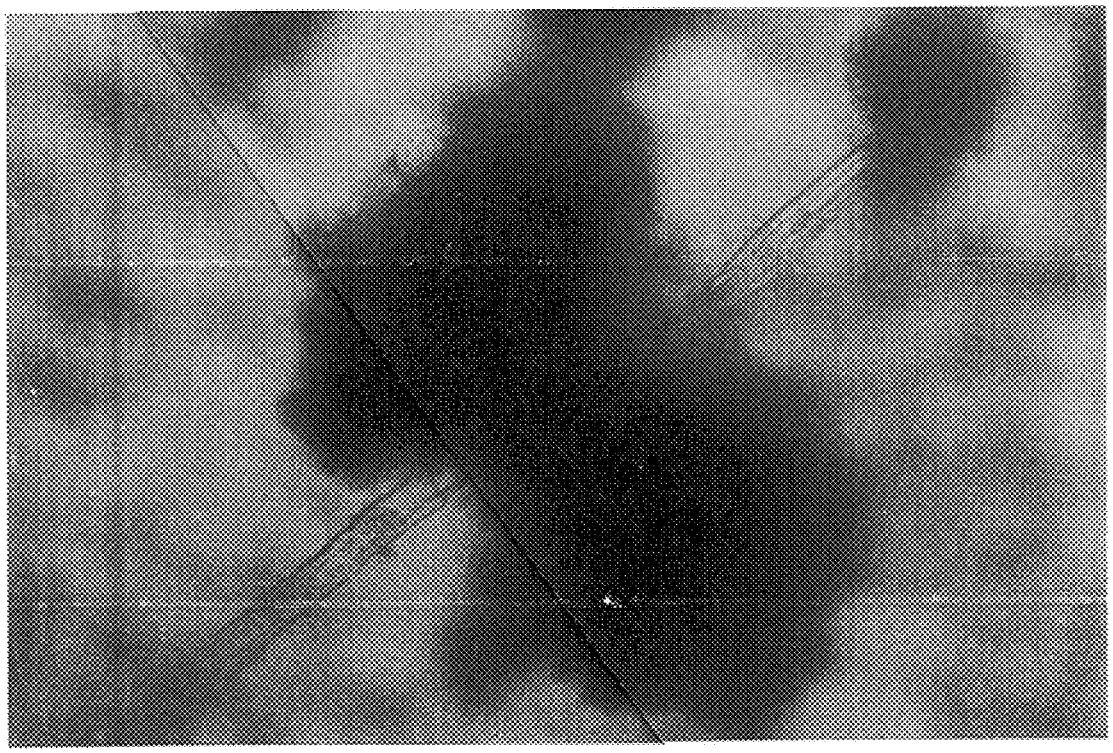
Figure 20D:
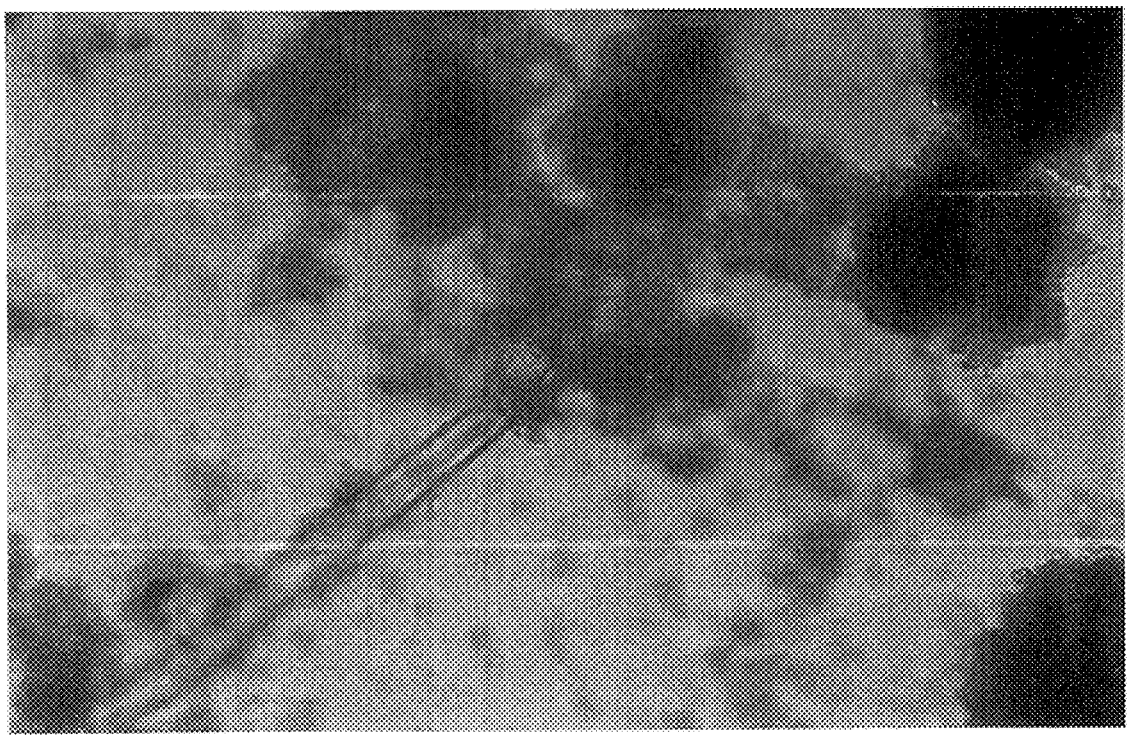

FIGS. 20A–D depict the survival, regeneration and neurite outgrowth of myelinated nerve fiber from the in vitro-isolated anterior horn motoneurons as originally shown in FIG. 17 (plate 5), FIG. 18 (plate 5), and FIG. 19 (plate 1), respectively, after 21 days of co-culture with the hrMNTF1-F6 protein with the GST moiety removed via thrombin proteolysis. FIG. 20A illustrates a low magnification photomicrograph (100×) of two separate motoneurons (one~1.5 mm in length and one~3 mm in length) which were regenerated from the cultured, in vitro-isolated anterior horn motoneurons. FIG. 20B depicts a low magnification (140×) photomicrograph of the motoneurons originally illustrated in plate 1 as well as a composite photomicrograph which illustrates the myelinated, regenerated neuron with oligodendrocytes (putative Schwann cells) attached. FIGS. 20C and 20D illustrate high magnification (400×) photomicrographs which revel the axonal cylinders in the inner regenerated myelinated nerve fiber with several Nodes of Rannier clearly depicted.

Amino Acid Sequencing of the Human Recombinant MNTF1-F3 and MNTF1-F6 Proteins

Figure 2B:
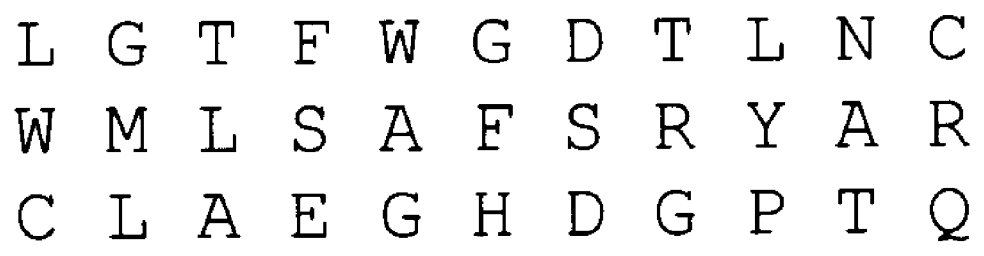

The amino acid sequence of the human recombinant MNTF1-F3 and MNTF1-F6 proteins were elucidated by direct protein sequencing methodologies. Prior to sequencing, the proteins were purified into non-fusion form via the aforementioned GST-monoclonal affinity column chromatography. The amino acid sequence of the MNTF1-F3 protein [SEQ ID NO:3] is shown in FIG. 2A. The amino acid sequence of the MNTF1-F6 protein [SEQ ID NO:4] is shown in FIG. 2B. By standard convention, the amino acid sequences are reported from the amino (NH2-) terminus to the carboxyl (—COOH) terminus.

PREPARATION OF MNTF FOR DRUG DELIVERY

The MNTFs of the present invention can thus be readily utilized in pharmacological applications. In vivo applications include administration of the factors to mammalian subjects and, in particular, to human subjects. The MNTFs may be administered orally or by injection, with the preferred mode being topical application on or near the affected motoneuron.

The pharmacological compositions of the present invention are prepared in conventional dosage unit forms by the incorporation of one or more of the MNTFs with an inert, non-toxic pharmaceutical "carrier" moiety according to accepted methodologies, in a non-toxic concentration sufficient to produce the desired physiological activity in a mammal and, in particular, a human subject. Preferably, the composition contains the active ingredient in a biologically-active, but non-toxic, concentration selected from a concentration of approximately 5 ng to 50 μg of active ingredient per dosage unit (e.g., per kg subject body weight). The concentration utilized will be dependent upon such factors as the overall specific biological activity of the ingredient, specific biological activity desired, as well as the condition and body weight of the subject.

The pharmaceutical carrier or vehicle employed may be, for example, a solid or liquid and a variety of pharmaceutical forms may be employed. Thus, when a solid carrier is utilized, the preparation may be plain milled, micronized in oil, tabulated, placed in a hard gelatin or enterically-coated capsule in micronized powder or pellet form, or in the form of a troche, lozenge, or suppository. The solid carrier, containing the MNTF, can also be ground up prior to use.

When utilized in a liquid carrier, the preparation may be in the form of a liquid, such as an ampule, or as an aqueous or non-aqueous liquid suspension. For topical administration, the active ingredient may be formulated using bland, moisturizing bases, such as ointments or creams. Examples of suitable ointment bases include, but are not limited to, petrolatum plus volatile silicones, lanolin, and water in oil emulsions such as Eucerin® (Beiersdorf). Examples of suitable cream bases include, but are limited to, Nivea Creams® (Beiersdorf), cold cream (USP), Purpose Cream® (Johnson & Johnson), hydrophilic ointment (USP), and Lubriderm® (Warner-Lambert).

Additionally, with respect to the present invention, the active ingredient may be applied internally at or near the site of the affected motoneuron. For example, a solid or gelled medium which is sufficiently permeable to allow the release of the active ingredient, preferably in a timed-release manner, may be utilized for such internal application. Examples of such gels include, but are not limited to, hydrogels such as polyacrylamide, agarose, gelatin, alginate, or other polysaccharide gums. Furthermore, the active ingredient may be imbedded in a solid material, such as filter paper, which is capable of absorbing and subsequently releasing the active ingredient, at the appropriate time and location.

While embodiments and applications of the present invention have been described in some detail by way of illustration and example for purposes of clarity and understanding, it would be apparent to those individuals whom are skilled within the relevant art that many additional modifications would be possible without departing from the inventive concepts contained herein. The invention, therefore, is not to be restricted in any manner except in the spirit of the appended claims.

What is claimed is:

1. An isolated polynucleotide encoding a polypeptide consisting of an amino acid sequence according to SEQ ID NO:4.

2. An expression vector operably linked to the isolated polynucleotide according to claim 1, where the open reading frame is operably linked to a control sequence compatible with a desired host vector.

3. An isolated host cell transformed with the expression vector of claim 2.

4. An isolated polynucleotide consisting of a sequence according to SEQ ID NO:2.

5. An expression vector operably linked to the isolated polynucleotide according to claim 4, where the open reading frame is operably linked to a control sequence compatible with a desired host vector.

6. A host cell transformed with the recombinant molecule of claim 5.

7. An isolated polynucleotide consisting of a sequence according to SEQ ID NO:5.

8. An expression vector operably linked to the isolated polynucleotide according to claim 7, where the open reading frame is operably linked to a control sequence compatible with a desired host vector.

9. An isolated host cell transformed with the expression vector of claim 8.

10. An isolated polynucleotide fully complementary to a polynucleotide encoding a polypetide consisting of an amino acid sequence according to SEQ ID NO:4.

11. An isolated polynucleotide consisting of a sequence fully complementary to SEQ ID NO:2.

12. An isolated polynucleotide consisting of a sequence fully complementary to SEQ ID NO:5.

\* \* \* \* \*

SEQUENCE LISTING

<160> NUMBER OF SEQ ID NOS: 5

<210> SEQ ID NO 1
<211> LENGTH: 1443
<212> TYPE: DNA
<213> ORGANISM: Homo sapiens

<400> SEQUENCE: 1

| | | | | | |
|---|---|---|---|---|---:|
| cgggcttatt | attccactga | tgagaacctg | atcctttccc | cactcctggg | taacgtctgc | 60 |
| ttctccagct | cccagtacag | catctgcttc | acgctgggct | cctttgccaa | gatctatgcc | 120 |
| gacacctttg | gtgacattaa | ttaccaagaa | tttgctaaaa | gactctgggg | tgacatctac | 180 |
| ttcaaccta | agacgcgaaa | gttcaccaaa | aaggcccca | ctagcagctc | ccagagaagt | 240 |
| ttcgtggagt | ttatcttgga | gcctctttat | aagatcctcg | cccaggttgt | aggtgacgtg | 300 |
| gacaccagcc | tcccacggac | cctagacgag | cttggcatcc | acctgacgaa | ggaggagctg | 360 |
| aagctgaaca | tccgccccctt | gctcaggctg | tctgcaaaa | agttcttttgg | cgagttcaca | 420 |
| ggctttgtgg | acatgtgtgt | gcagcatatc | ccttctccaa | aggtgggcgc | caagcccaag | 480 |
| attgagcaca | cctacaccgg | tggtgtggac | tccgacctcg | gcgaagctat | gagtgactgt | 540 |
| gaccctgatg | gcccctgat | gtgccacact | actaagatgt | tcagcacaca | tgatggagtc | 600 |
| cagtttcacc | cctttggccg | ggtgctgagt | ggcaccattc | atgctgggca | gcctgtgaag | 660 |
| gttctggggg | agaactacac | cctggaggat | gaggaagact | ccccaatttg | ccccgtgggc | 720 |
| cgcctttgga | tctctgtggc | cagctaccac | atcgaggtga | accgtgttcc | tgctggcaac | 780 |
| tgggttctga | ttgaaggtgt | tgatcaacca | attgtgaaga | cagcaaccat | aaccgaaccc | 840 |
| cgaggcaatg | aggaggctca | gattttccga | cccttgaagt | tcaataccac | atctgttatc | 900 |
| aagattgctg | tggagccagt | caaccccctca | gagctgccca | agatgcttga | tggcctgcgc | 960 |
| aaggtcaaca | gagctatcc | atccctcacc | accaaggtgg | aggagtctgg | cgagcatgtg | 1020 |
| atcctgggca | ctggggagct | ctacctggac | tgtgtgatgc | atgatttgcg | gaagatgtac | 1080 |
| tcagagatag | acatcaaggt | ggctgaccca | gttgtcacgt | tttgtgagac | ggtcgtggaa | 1140 |
| acatcctccc | tcaagtgctt | tgctgaaacg | cctaataaga | agaacaagat | caccatgatt | 1200 |
| gctgagcctc | ttgagaaggg | cctggcagag | gacatagaga | atgaggtggt | ccagattacg | 1260 |
| tggaacagga | agaagctggg | agagttcttc | cagaccaagt | acgattggga | tctgctggct | 1320 |
| gcccgttcca | tctgggcttt | tggccctgat | gcgactggcc | ccaacattct | ggtggatgat | 1380 |
| actctgccct | ctgaggtgga | caaggctctt | cttggttcag | tgaaggacag | catcgttcaa | 1440 |
| ggt | | | | | | 1443 |

<210> SEQ ID NO 2
<211> LENGTH: 927
<212> TYPE: DNA
<213> ORGANISM: Homo sapiens

<400> SEQUENCE: 2

| | | | | | |
|---|---|---|---|---|---:|
| ttggggacat | tttgggggtga | cacactgaac | tgctggatgc | tatcagcatt | tagtaggtat | 60 |
| gctcgatgtc | ttgcagaagg | acatgatggt | cctacacagt | aaggaatgga | ttacctacaa | 120 |
| tattaatagc | agcctcccat | acacactttt | gacacccttc | cctaaaggat | taatatgctc | 180 |
| caaccttcct | gtccccacag | ttcagtggct | ctccctaccc | tcaccatgat | cggatgaaaa | 240 |
| aaaataaggt | ttcacagctt | aagagtgaaa | ttctggaatc | caactacaag | ctcataactg | 300 |

```
tagcatggaa cctggtagta gcataataaa taaattttta gtaagaggct taagaaattt    360
tagcaaaaaa agcactccct ttcttcctcc ctacatatct catatgtttt tcaacacaaa    420
aaattctgtg attttagaga aacttcttac agtacttta agttcaaaac cagatgctca     480
ttacagttct tttaaacacc aaactagtca tctcaaaaat atggctaact ctctggacta    540
aattccatag gaaaaattat taatttcaaa atgcctaatt tttgatcaat gctgaagagc    600
caagcaatca tgtcctgctt ctcactcagg gcagagttct caggtcagaa gctccggagt    660
ctgtcagaga ttaaaatatc atctcaacaa ttcacaagct acttctaagt gttaccctaa    720
attagtcact aatcgtttct cccccaactc tatttcacaa attaaagttt acagaattga    780
caaaaaccaa accaatgaaa caacccaggc tatttgcagg ggggggaaa gagataccc     840 aaaagtcaac cctatttaca cgtagttaaa agagtgatcc aacagatatt accctccata    900
aagtacctaa aggcaggagc cggaatt                                       927
```

<210> SEQ ID NO 3
<211> LENGTH: 481
<212> TYPE: PRT
<213> ORGANISM: Homo sapiens

<400> SEQUENCE: 3

```
Arg Ala Tyr Tyr Ser Thr Asp Glu Asn Leu Ile Leu Ser Pro Leu Leu
 1               5                  10                  15

Gly Asn Val Cys Phe Ser Ser Gln Tyr Ser Ile Cys Phe Thr Leu
            20                  25                  30

Gly Ser Phe Ala Lys Ile Tyr Ala Asp Thr Phe Gly Asp Ile Asn Tyr
        35                  40                  45

Gln Glu Phe Ala Lys Arg Leu Trp Gly Asp Ile Tyr Phe Asn Pro Lys
    50                  55                  60

Thr Arg Lys Phe Thr Lys Lys Ala Pro Thr Ser Ser Gln Arg Ser
 65                  70                  75                  80

Phe Val Glu Phe Ile Leu Glu Pro Leu Tyr Lys Ile Leu Ala Gln Val
                85                  90                  95

Val Gly Asp Val Asp Thr Ser Leu Pro Arg Thr Leu Asp Glu Leu Gly
            100                 105                 110

Ile His Leu Thr Lys Glu Glu Leu Lys Leu Asn Ile Arg Pro Leu Leu
        115                 120                 125

Arg Leu Val Cys Lys Lys Phe Phe Gly Glu Phe Thr Gly Phe Val Asp
    130                 135                 140

Met Cys Val Gln His Ile Pro Ser Pro Lys Val Gly Ala Lys Pro Lys
145                 150                 155                 160

Ile Glu His Thr Tyr Thr Gly Gly Val Asp Ser Asp Leu Gly Glu Ala
                165                 170                 175

Met Ser Asp Cys Asp Pro Asp Gly Pro Leu Met Cys His Thr Thr Lys
            180                 185                 190

Met Phe Ser Thr His Asp Gly Val Gln Phe His Pro Phe Gly Arg Val
        195                 200                 205

Leu Ser Gly Thr Ile His Ala Gly Gln Pro Val Lys Val Leu Gly Glu
    210                 215                 220

Asn Tyr Thr Leu Glu Asp Glu Asp Ser Gln Ile Cys Thr Val Gly
225                 230                 235                 240

Arg Leu Trp Ile Ser Val Ala Arg Tyr His Ile Glu Val Asn Arg Val
                245                 250                 255
```

```
Pro Ala Gly Asn Trp Val Leu Ile Glu Gly Val Asp Gln Pro Ile Val
            260                 265                 270

Lys Thr Ala Thr Ile Thr Glu Pro Arg Gly Asn Glu Glu Ala Gln Ile
        275                 280                 285

Phe Arg Pro Leu Lys Phe Asn Thr Ser Val Ile Lys Ile Ala Val
        290                 295                 300

Glu Pro Val Asn Pro Ser Glu Leu Pro Lys Met Leu Asp Gly Leu Arg
305                 310                 315                 320

Lys Val Asn Lys Ser Tyr Pro Ser Leu Thr Thr Lys Val Glu Glu Ser
                325                 330                 335

Gly Glu His Val Ile Leu Gly Thr Gly Glu Leu Tyr Leu Asp Cys Val
                340                 345                 350

Met His Asp Leu Arg Lys Met Tyr Ser Glu Ile Asp Ile Lys Val Ala
            355                 360                 365

Asp Pro Val Val Thr Phe Cys Glu Thr Val Val Glu Thr Ser Ser Leu
    370                 375                 380

Lys Cys Phe Ala Glu Thr Pro Asn Lys Lys Asn Lys Ile Thr Met Ile
385                 390                 395                 400

Ala Glu Pro Leu Glu Lys Gly Leu Ala Glu Asp Ile Glu Asn Glu Val
                405                 410                 415

Val Gln Ile Thr Trp Asn Arg Lys Lys Leu Gly Glu Phe Phe Gln Thr
            420                 425                 430

Lys Tyr Asp Trp Asp Leu Leu Ala Ala Arg Ser Ile Trp Ala Phe Gly
            435                 440                 445

Pro Asp Ala Thr Gly Pro Asn Ile Leu Val Asp Thr Leu Pro Ser
    450                 455                 460

Glu Val Asp Lys Ala Leu Leu Gly Ser Val Lys Asp Ser Ile Val Gln
465                 470                 475                 480

Gly

<210> SEQ ID NO 4
<211> LENGTH: 33
<212> TYPE: PRT
<213> ORGANISM: Homo sapiens

<400> SEQUENCE: 4

Leu Gly Thr Phe Trp Gly Asp Thr Leu Asn Cys Trp Met Leu Ser Ala
 1               5                  10                  15

Phe Ser Arg Tyr Ala Arg Cys Leu Ala Glu Gly His Asp Gly Pro Thr
            20                  25                  30

Gln

<210> SEQ ID NO 5
<211> LENGTH: 99
<212> TYPE: DNA
<213> ORGANISM: Homo sapiens

<400> SEQUENCE: 5
ttggggacat tttggggtga cacactgaac tgctggatgc tatcagcatt tagtaggtat      60
gctcgatgtc ttgcagaagg acatgatggt cctacacag                            99
```